United States Patent
Savino et al.

(10) Patent No.: US 6,641,807 B1
(45) Date of Patent: Nov. 4, 2003

(54) ADENOVIRAL VECTORS ENCODING ERYTHROPOIETIN AND THEIR USE IN GENE THERAPY

(75) Inventors: Rocco Savino, Pomezia (IT); Gennaro Ciliberto, Pomezia (IT); Nicola La Monica, Pomezia (IT)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/762,668

(22) PCT Filed: Aug. 5, 1999

(86) PCT No.: PCT/EP99/05661

§ 371 (c)(1),
(2), (4) Date: Apr. 23, 2001

(87) PCT Pub. No.: WO00/09713

PCT Pub. Date: Feb. 24, 2000

(30) Foreign Application Priority Data

Aug. 13, 1998 (GB) ................................. 9817660

(51) Int. Cl.[7] .................... A01N 63/00; A61K 48/00
(52) U.S. Cl. ................. 424/93.2; 435/320.1; 435/455; 435/456
(58) Field of Search .............. 435/320.1, 455, 435/456; 514/44; 424/93.2

(56) References Cited

U.S. PATENT DOCUMENTS 6,001,557 A * 12/1999 Wilson et al. ................. 435/5

FOREIGN PATENT DOCUMENTS

| WO | WO 95/29993 | 11/1995 |
| WO | WO 96/13598 | 5/1996 |
| WO | WO 97/32481 | 9/1997 |

OTHER PUBLICATIONS

FH Martini, Anatomy & Physiology, Simon and Schuster, Co., 3rd Ed. 1995, pp. 641 and 660.*
G Schiedner et al., Nature Genetics, "Genomic DNA transfer with a high-capacity adenovirus vector results in improved in vivo gene expression and decreased toxicity," Feb. 1998, vol. 18, pp. 180–183.*
C–K Kim et al., Arch Pharm Res., "Gene Medicine: A New Field of Molecular Medicine," 2001, vol. 24, No., 1, pp. 1–15.*
N Morral et al., Human Gene Therapy, "High Doses of a Helper–Dependent Adenoviral Vector Yield Supraphysiological Levels of 1–Antitrypsin with Negligible Toxicity," Dec. 1998, 9: 2709–2716.*
Kim et al., Gene Medicine: A new field of molecular medicine, 2001, ARCH. PHARM. RES., vol. 24, pp. 1–15.*
Anderson, Human gene therapy, 1998, NATURE, vol. 392, pp. 25–30.*

Verma et al., Gene therapy–promises, problems and prospects, 1997, NATURE, vol. 389, pp. 239–242.*
Chen et al., Persistance in muscle of an adenoviral vector that lacks all viral genes, 1997, PROC. NATL. ACAD. SCI. USA, vol. 94, pp. 1645–1650.*
Malone et al., An improved helper–dependent adenoviral vector allows persistent gene expression after intramuscular delivery and overcomes preexisting immunity to adenovirus, 2001, PNAS, vol. 98, pp. 5986–5991.*
Chen et al., DNA from both high–capacity and first–generation adenoviral vectors remains intact in skeletal muscle, 1999, HUMAN GENE THERAPY, vol. 10, pp. 365–373.*
Hardy et al., Construction of adenovirus vectors through cre–lox recombination, 1997, JOURNAL OF VIROLOGY, pp. 1842–1849.*
Morsy et al., Expanded–capacity adenoviral vectors–the helper–dependent vectors, 1999, ELSEVIER SCIENCE, pp. 18–24.*
Malone et al., Prolonged expression and effective readministration of erythropoietin delivered with a fully deleted adenoviral vector, 2000, HUMAN GENE THERAPY, vol. 11, pp. 859–868.*
Eck, The Prospects for gene therapy, 1999, MOLECULAR MEDICINE FOR CLINICIANS, pp. 1–12.*
Morsy, M. et al., An Adenoviral Vector Deleted For All Viral Coding Sequences Results In Enhanced Safety and Extended Expression of a Leptin Transgene, PROC NATL ACAD SCI USA vol. 95, pp. 7866–7871, Jul. 1998.
Kochanek, S. et al., A New Adenoviral Vector: Replacement of all Viral Coding Sequences . . . and β–Galactosidase, PROC NATL ACAD SCI, vol. 93, pp. 5731–5736, Jun. 1996.
Svensson, E. et al., Long–Term Erythropoietin Expression in Rodents and Non–Human Primates Following Intramuscular Injection of a Replication–Defective Adenoviral Vector, HUMAN GENE THERAPY, vol. 8, pp 1797–1806, Oct. 1997.
Descamps, V. et al., Erythropoietin Gene Transfer and Expression in Adult Normal Mice: Use of an Adenovirus Vector, HUMAN GENE THERAPY, vol. 5, pp 979–985, Aug. 1994.
Tripathy, S. Immune Responses to Transgene–Encoded Proteins Limit The Stability of Gene Expression After Injection of Replication–Defective Adenovirus Vectors, NATURE MED, vol. 2, No. 5, May 1996.

* cited by examiner

Primary Examiner—Scott D. Priebe
Assistant Examiner—Brian Whiteman
(74) Attorney, Agent, or Firm—Joan E. Switzer; Joanne M. Giesser

(57) ABSTRACT

Helper dependent adenoviral vectors encoding erythropoietin (epo) provide high levels of epo to achieve a long-term therapeutically effective dosage, and allow for repeat administration to patients with disorders such as anaemia of Chronic Renal Failure (CFR), anaemias due to beta-thalassaemia, and sickle cell anaemia (SCA).

4 Claims, 10 Drawing Sheets

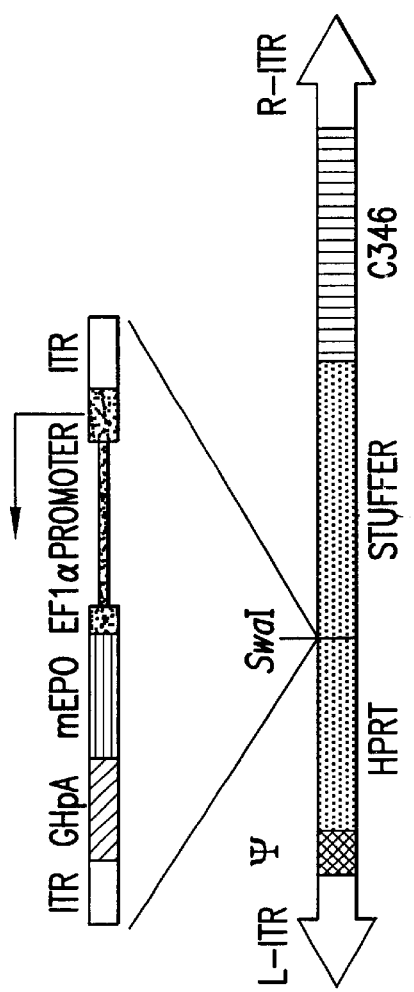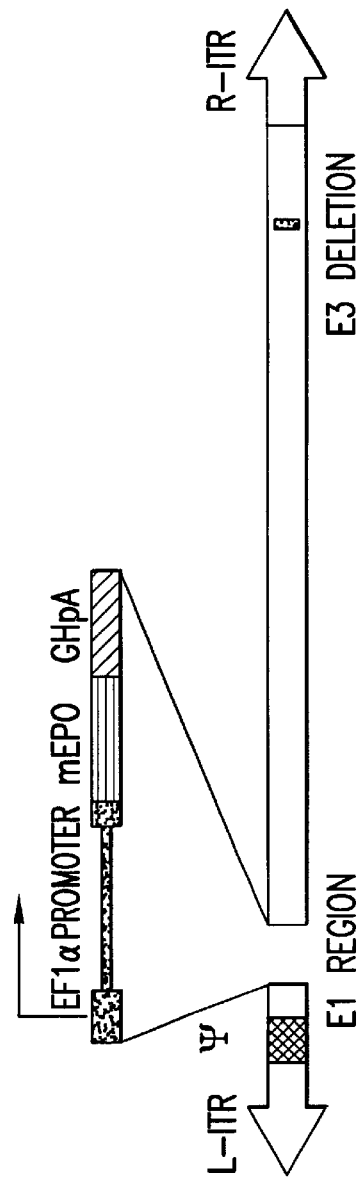

ADENOVIRAL VECTORS ENCODING ERYTHROPOIETIN AND THEIR USE IN GENE THERAPY

CROSS-REFERENCE TO RELATED APPLICATIONS

This application is a U.S. national application of PCT/US99/05661, filed Aug. 5, 1999, and which published as WO 00/09713, Feb. 24, 2000, and which claims the benefit of a Great Britain Patent Application No. 9817660.5, filed Aug. 13, 1998.

The present invention relates to the delivery of erythropoietin (EPO) to a mammal. More particularly, the present invention relates to provision of EPO in a mammal by means of expression from encoding nucleic acid included in an expression vector, that is by means of gene therapy. The present invention is based on the inventors' experimental demonstration that therapeutic levels of EPO can be achieved using helper-dependent adenoviral (Hd-Ad) vectors, which levels are far beyond any levels previously attained using a variety of vectors, including adenoviral (Ad) vectors (i.e. non-helper-dependent).

Erythropoietin (EPO) is a protein of great interest because of its therapeutic usefulness in a variety of diseases. As is well known, the gene for human EPO was cloned by Amgen (see e.g. WO85/02610, EP-A-0148605) and recombinantly produced EPO (rEPO) has attained a huge market (in excess of 2.9 billion dollars). Currently, rEPO is administered to patients in protein form.

Despite its success, there is a number of problems with delivery of rEPO resulting in various unmet clinical needs, primarily because of the prohibitive cost of providing sufficient rEPO to achieve a long-term therapeutically effective dosage. Sufferers include individuals with anaemia of Chronic Renal Failure (CRF), anaemias due to beta-thalassaemia, and sickle cell anaemia (SCA). Large numbers of such individuals go untreated despite the fact that good therapeutic results can be achieved as long as enough EPO is provided.

In CRF there is an irreversible decline of kidney function, and the patients manifest a sequel of renal dysfunctions, including anaemia, but do not necessarily require dialysis except at the end stage renal disease (ESRD). At this stage the patient require either regular dialysis or kidney transplant.

CRF patients may be treated with rEPO, such treatment involving starting doses of 50–100 U/Kg, three times weekly, to achieve an increment of at least 5–6 point in the haematocrit. (Note that in vivo bioactivity of EPO is generally determined by the simple measurement of increase in haematocrit (Hct) by centrifugation of heparinsed blood in capillary tubes.) If this is not achieved within 8 weeks, the dose needs to be increased. Maintenance doses need to be individualised (Hct increase over 48%, are possibly deadly), with average of 75 U/Kg three times weekly, but ranging from 12.5 to 525 U/Kg three times weekly.

Circulating rEPO half life is of 4–13 hours if administered i.v., or 25–30 hours after s.c. administration. Over 95% of CRF patients respond well to the treatment, with a measurable Hct increase, and all are reported to become transfusion-independent after 2 months of treatment.

In both beta-thalassaemia and sickle cell anaemia the formation of a normal $\alpha_2\beta_2$ haemoglobin (Hb) is impaired. Studies in baboons demonstrate that large doses (800–9,000 U/kg i.v.) of recombinant human EPO given i.v. increase gamma-globin chain synthesis and foetal Hb (AL-Khatt et al., N. En. J. Med., 1987, 317: 415–420).

Clinical trials with rEPO in SCA and beta-thalassaemia, with average doses of 500–1500 U/kg, show a rise in RBC count, Hb content and Hct. In SCA a significant increase of foetal Hb correlates with improved quality of RBC, reduced sickling episodes and improved quality of life.

There is no report of the insurgence of anti-EPO antibodies in CRF patients, even those treated for over 4 years, nor in patients with SCA or beta-thalassaemia.

What denies many individuals rEPO treatment is the costs of providing so much: $\geq 1,500$ U/kg is required three times weekly for significant Hct increase and induction of $\gamma$-globulin synthesis in SCA patients.

The provision of an effective system for delivery of sufficient EPO would have ready application given the proven therapeutic effectiveness of the protein in diseases such as those discussed above.

The dosage of biologically active circulating EPO required to reach the therapeutic window for Hb-F stimulation is believed to be in excess of 0.900 U/ml (given that >1,5000 U/Kg three times weekly is necessary, and that the half life of EPO administered s.c. is 18 hrs). To date, despite many attempts using numerous approaches, there has been no report of such a level being achieved using a gene therapy approach, i.e. delivery of EPO by means of expression in the body from encoding nucleic acid conveyed within a recombinant vector.

Delivery of EPO cDNA by different means are described in the prior art. The highest level of circulating EPO reported is around 0.75 U/ml (Kessler P. D. et al. 1996, PNAS 93, 14082–7), well below the level required to have beneficial effect in SCA or beta-thalassaemia.

Studies have been published by other laboratories using Adeno vectors carrying the EPO gene which have shown limitations of these vectors in providing appropriate gene dosage and controlled hormonal release over a prolonged period of time.

Descamp et al., (1994, Human Gene Therapy 5:979–985) used an adenovector containing monkey EPO cDNA under the control of an RSV-LTR promoter. A minimum of $5 \times 10_9$ viral PFUs (plaque forming units) were required to give Hct increase (observed in a subset of animals). Example 15 below includes a comparison of results achieved using an embodiment of the present invention with results of Descamp et al.

Svensson et al. (1997, Human Gene Therapy 8:1797–1806) used an adenovector containing a mouse EPO coding sequence operably linked to an EF1α promoter, injecting particles i.m. Maximal EPO levels with $10^9$ PFUs/mouse was 90 mU/m. No real dose response was shown. The same group earlier published Tripathy et al., 1996 Nat Med., 2: 545–50, and Tripathy et al., 1996 PNAS USA 93, 10876–80, in the latter of which naked DNA was injected into muscle, the maximal EPO levels achieved in blood being 50 mU/ml. The minimal amound of naked DNA needed to observed Hct increase was 10 mg/mouse, 500 mg/kg, corresponding to 35 mg/injection for a human of average 70 kg weight, a huge amount. Example 14 below includes comparison of results achieved using an embodiment of the present invention compared with the results of Svensson et al.

Remarkably, the experimental work described below demonstrates that use of embodiments of the present invention allows for circulating EPO levels of 300 U/ml to be achieved, i.e. far in excess of the level required for effective therapy. Furthermore, these levels can be obtained following a single injection and sustained over long periods of time.

The present invention in various aspects and embodiments employs an EPO encoding sequence within an adenovirus vector in which the entire Adenoviral genome coding sequences have been removed and substituted with exogenous DNA stuffer sequences, generally a Helper-Dependent Adenovirus vector (Hd-Ad).

A general aspect of the present invention provides for the use of such an adenoviral vector in delivery of erythropoietin to an individual. Such delivery is especially at a level in the serum of the individual of at least about 0.005, or 0.1, or 0.5, or 1, or 2, or 3, or 4, or 5, or 6, or 7, or 8, or 9, or 10 U/ml, and may be greater than about 10 U/ml, such as about 20, 30, 40 or 50 U/ml. As noted, levels of up to 300 U/ml are achievable using embodiments of the present invention.

One unit (U) of EPO corresponds approximately to 10 ng of pure protein and can be defined with reference to the international standard WHO-EPO 2nd International Reference Preparation (Annable et al., 1972, Bull. Wld, Hlth. Org. 47: 99) as the amount that is required to produce equivalent [$^3$H]-thymidine incorporation into spleen cells from phenylhydrazine-treated mice to that expressed by 1 unit of the WHO standard preparation, or the amount needed to induce 50% of maximum growth (FC50) in erythroleukaemia cells, TF1.

One advantage that may be attained using the present invention is a dose response curve, making it possible to calculate the amount of vector to administer to achieve a desired level of circulating EPO.

One aspect of the present invention provides a method of delivering erythropoietin (EPO) to an individual, the method including provision in the individual of an adenoviral vector ad disclosed including nucleic acid encoding erythropoietin operably linked to regulatory sequences for production of erythropoietin in the individual by expression from the nucleic acid, especially whereby on such expression a dosage of erythropoietin at a level as indicated.

A further aspect of the present invention provides an adenoviral vector as disclosed including nucleic acid encoding erythropoietin operably linked to regulatory sequences for production of erythropoietin by expression from the nucleic acid. Such a vector may be provided for use in delivery of erythropoietin to an individual, especially for delivery of erythropoietin at a level in the serum of the individual as indicated.

A still further aspect of the present invention provides the use of an adenoviral vector as disclosed including nucleic acid encoding erythropoietin operably linked to regulatory sequences for production of erythropoietin by expression from the nucleic acid, in the manufacture of a medicament for delivery of erythropoietin to an individual, especially to the serum at a level as indicated.

A feature of embodiments of the present invention is the opportunity for repeat administration. Adenoviral vectors according to the invention may be re-administered to an individual to which such a vector (e.g. even of the same serotype) has previously been administered, e.g. at or more than about one month, e.g. 35 days, preferably at or more than about two months, more preferably at or more than about three months, more preferably at or more than about four months, more preferably at or more than about six months, more preferably at or more than about nine months, more preferably at or more than about 12 months, more preferably at or more than about 18 months, more preferably at or more than about 24 months from the first, or previous, administration. The re-administration may result in equivalent or greater levels of erythropoietin in the serum and/or increase in haematocrit.

The present invention allows for delivery of erythropoietin to achieve stable elevated levels in the serum.

For each aspect, either in addition to provision in the serum at at least the indicated level or alternatively, the provision may be for delivery of erythropoietin for an increase in the haematocrit reading of about 5%, or about 10%, or about 15%, or about 20%. The level of haematocrit may reach about 30%, or about 35%, or about 40%, or about 45%, or about 50%. For instance an increase of 10–15% on a reading of 30% for an anaemic level, i.e. to physiological levels of around 40–45%, may be achieved.

The level of erythropoietin and/or increase in haematocrit may be maintained to at least about 70%, more preferably at least about 80%, more preferably at least about 90%, more preferably at least about 95% of the level attained (that is attained following the first or previous administration) for at least about one month, preferably at least about two months, e.g. at least 84 days, more preferably at least about three months, more preferably at least about four months, e.g. at least 140 days, more preferably at least about six months, more preferably at least about nine months, more preferably at least about 12 months, more preferably at least about 18 months, more preferably at least about 24 months from the first, or previous, administration.

The individual may have a disease or disorder such that delivery of erythropoietin is of benefit or has a therapeutically beneficial effect. Delivery of erythropoietin may ameliorate one or more symptoms of the disease or disorder.

Diseases and disorders that may be treated in accordance with the present invention include anaemia of Chronic Renal Failure (CRF), anaemias due to beta-thalassaemia, and sickle cell anaemia (SCA), other anaemias including following radiation therapy or chemotherapy.

As indicated by the experiments included below, such high levels of expression may be achieved using embodiments of the present invention (e.g. using the EF1α promoter) that an excess of EPO may be delivered, which may result in side-effects in certain situations or individuals.

In SCA and in beta-thalassaemia it appears that excess production of EPO would not be detrimental, because even at very high EPO level, the maximum production of foetal-Hb is naturally limited and will not result in a dangerous increase of the Hct.

For delivery in other situations, e.g. for treatment of CRF patients, some more stringent regulation of gene expression may be employed, e.g. using a different promoter.

Parks et al. (1996). Proc. Natl. Acad. Sci. USA 93:13656–13570 describes a convenient packaging system for the large scale preparation of Helper-Dependent adenovirus vectors. In this system the Helper-Dependent vector is transfected in 293Cre cells, stably expressing the Cre recombinase. The cells are infected with the Helper Adenovirus, which furnishes in trans all the functions needed for the vector replication and packaging. The packaging signal of the Helper Adenovirus is flanked by two lox P sites, which are recognized by the Cre recombinase expressed in 293Cre cells: the packaging signal is thus removed and the majority of the Helper Adenovirus genomes cannot be packed, leading to preferential packaging of the Vector. After full cytopathic effect is obtained, the crude lysate is used to infect fresh 293Cre cells, coinfected with Helper Adenovirus: repeated cycles of infection bring to amplification of the vector. Roughly 20% of the Helper Adenovirus genomes escape Cre-mediated packaging signal excision, leading to the generation of a small amount of Helper Adenovirus. This small amount of contaminant can be easily removed by CsCl buoyant density centrifugation, leading to packaged helper-dependent vector preparations which are highly purified, with less that 0.1% helper Adenovirus contamination (Parks et al., 1996).

Suitable vectors may include the pSTK120 backbone employed by Morsy et al. (July 1998) PNAS USA 95: 7866–7871 in a HD-Ad vector for delivery of a leptin transgene to ob/ob mice.

The erythropoietin encoding sequence may be placed within the vector in any site that operably links it to the regulatory sequences for expression whereby the indicated level of erythropoietin and/or increase in haematocrit is achieved on expression in an individual. Suitable cloning sites are SWA I (NT 8096), EAG I (NT 16520), FSE I (NT 25653), SRf I (NT 14735), EcoRI (NT 24916, BspEI (NT 24321).

The regulatory sequences for expression will include a promoter.

By "promoter" is meant a sequence of nucleotides from which transcription may be initiated of DNA operably linked downstream (i.e. in the 3' direction on the sense strand of double-stranded DNA).

"Operably linked" means joined as part of the same nucleic acid molecule, suitably positioned and oriented for transcription to be initiated from the promoter. DNA operably linked to a promoter is "under transcriptional initiation regulation" of the promoter.

Other regulatory sequences including terminator fragments, polyadenylation sequences, enhancer sequences, marker genes and other sequences may be included as appropriate, in accordance with the knowledge and practice of the ordinary person skilled in the art: see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Ausubel et al. eds., John Wiley & Sons, 1992.

As noted, different promoters and other regulatory sequences may drive production of erythropoietin with different levels of promoter activity.

"Promoter activity" is used to refer to ability to initiate transcription. The level of promoter activity is quantifiable for instance by assessment of the amount of mRNA produced by transcription from the promoter or by assessment of the amount of protein product produced by translation of mRNA produced by transcription from the promoter, for instance by determining protein activity or evidence of protein activity (such as for erythropoietin an increase in haematocrit in an individual). The amount of a specific mRNA present in an expression system may be determined for example using specific oligonucleotides which are able to hybridise with the mRNA and which are labelled or may be used in a specific amplification reaction such as the polymerase chain reaction. Use of a reporter gene facilitates determination of promoter activity by reference to protein production.

EPO units (U/ml) may be assayed using the Quantikine IVD rhEpo ELISA kit of Accurate Chemical & Scientific, Minneapolis, Minn., USA, which is calibrated by the manufacturer against the international standard WHO-EPO 2nd International Reference Preparation (Annable et al., 1972, Bull. Wld, Hlth. Org. 47: 99).

Suitable promoters for use in aspects and embodiments of the present invention include the human elongation factor 1α (EF1α) promoter, viral promoters such as CMV or RSV promoters, promoters linked to tet operator sequences, promoters linked to GAL4 binding sites, hypoxia inducible promoters, such as the Hypoxia Responsive Elements (HRE) naturally found in the erythropoietin gene.

Adenoviral particles containing nucleic acid encoding erythropoietin produced in accordance with the present invention may be formulated in pharmaceutical compositions. These compositions may comprise a pharmaceutically acceptable excipient, carrier, buffer, stabiliser or other materials well known to those skilled in the art. Such materials should be non-toxic and should not interfere with the efficacy of the active ingredient. The precise nature of the carrier or other material may depend on the route of administration, e.g. intravenous, cutaneous or subcutaneous, nasal, intramuscular, intraperitoneal routes.

Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Following production of adenoviral particles according to the invention and optional formulation of such particles into compositions, the particles may be administered to an individual, particularly human or other primate. Administration may be to another mammal, e.g. rodent such as mouse, rat or hamster, guinea pig, rabbit, sheep, goat, pig, horse, cow, donkey, dog or cat.

This may be for a therapeutic purpose, e.g. in delivery of a functional gene encoding an authentic biologically active product in a method of gene therapy, to treat a patient who is unable to synthesize that product or unable to synthesize it at the normal level or in normal form, thereby providing the effect provided by the wild-type and ameliorating one or more symptoms of the relevant disease.

Administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors, or in a veterinary context a veterinarian, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980.

The number of Adenovector particles to be administered in accordance with the present invention may be from around $1\times10^3$/g to about $1\times10^6$/g body weight, and may be about $1\times10^3$, or about $1\times10^5$, or about $1\times10^6$, preferably about $1\times10^4$/g body weight. Embodiments of the present invention allow for delivery of lower numbers of particles to be administered compared with work described in the prior art noted above, e.g. less than $1\times10^9$, more preferably less than $1\times10^8$.

A composition may be administered alone or in combination with other treatments, either simultaneously or sequentially dependent upon the condition to be treated. For example, in the case of SCA treatment may be in combination with hydroxyurea.

Delivery to a non-human mammal need not be for a therapeutic purpose, but may be for use in an experimental context. The erythropoietin for administration to a mammal of interest is preferably the erythropoietin of that species (including modified forms thereof) or a related species. Thus, for example, human EPO will generally be used for administration to humans (much as in the experiments described below murine EPO was administered to mice).

Further aspects and embodiments of the present invention will be apparent to those of ordinary skill in the art, in view of the above disclosure and following experimental exemplification, included by way of illustration and not limitation, and with reference to the attached figures.

BRIEF DESCRIPTION OF THE FIGURES

FIG. 1 shows structures of HD(pSTK-ITR-mEPO)Ad and HVAd-mEPO viruses.

FIG. 1A illustrates HD(pSTK-ITR-mEPO)Ad, which is based on an STK-120 backbone (Morsy et al., 1998) containing, in the following order: the Ad5 inverted terminal repeat (L-ITR) and the packaging signal ($\psi$), 440 bp (nucleotides 1–440); a 16.054-bp fragment of hypoxanthine guanine phosphorybosyltransferase (HPRT stuffer, nucleotides 1.799–17.853 in gb:humhprtb); a HindIII 9,063-bp fragment of C346 cosmid (nucleotides 12.421–21.484 in gb:humhprtb); the right-end terminus of Ad5, composed of the ITR sequence, 117 bp (R-ITR: nucleotides 35.818–35.935). Total length of the STK-120 backbone is 25.674 bp. The 2.561-bp mEPO expression cassette is cloned in the unique SwaI site in the HPRT stuffer, bringing the size of HD-mEPO to 28.235-bp. ITR: Adeno-Associated Virus (AAV) Inverted Terminal Repeat; GHpA: bovine Growth Hormone gene polyadenylation signal. The intron contained in the EF1a promoter region is indicated by a thinner line.

FIG. 1B illustrates HVAd-mEPO, which is based on the backbone of pHVAd1, 35.321 bp. Homologous recombination inserted the 2.202-bp mEPO expression cassette (without the AAV ITRs), causing at the same time a 3.181-bp deletion (nucleotides 342–3.523) of E1 sequences. Total length of HVAd-mEPO is therefore 34.342 bp.

FIG. 3 shows in vivo comparison between hd(pSTK-ITR-mEPO)Ad and HVAd-mEPO. The viruses hd(pSTK-ITR-mEPO)Ad and HVAd-mEPO were infused side-by-side in the tail vein of healthy adult female BALB/c mice.

FIG. 4 shows mouse EPO and haematocrit levels in BALB/c mice. Groups of healthy adult female BALB/c mice (n=5) were infused in the tail vein with various doses of hd(pSTK-ITR-mEPO)Ad virus (from $3\times10^5$ to $8\times10^8$ transducing units).

FIG. 5 shows mouse EPO and haematocrit levels in DBA/2J and CD-1 mice. Groups of healthy adult female DBA/2J mice (n=6) were infused in the tail vein with various doses of hd(pSTK-ITR-mEPO)Ad virus (from $3\times10^5$ to $1\times10^7$ transducing units).

FIG. 7 shows results of experiments involving virus readministration a long time after the first injection.

FIG. 8 shows results of blood measurement after subtotal nephrectomy in rats.

EXPERIMENTAL INTRODUCTION AND DISCUSSION

Figure 2:
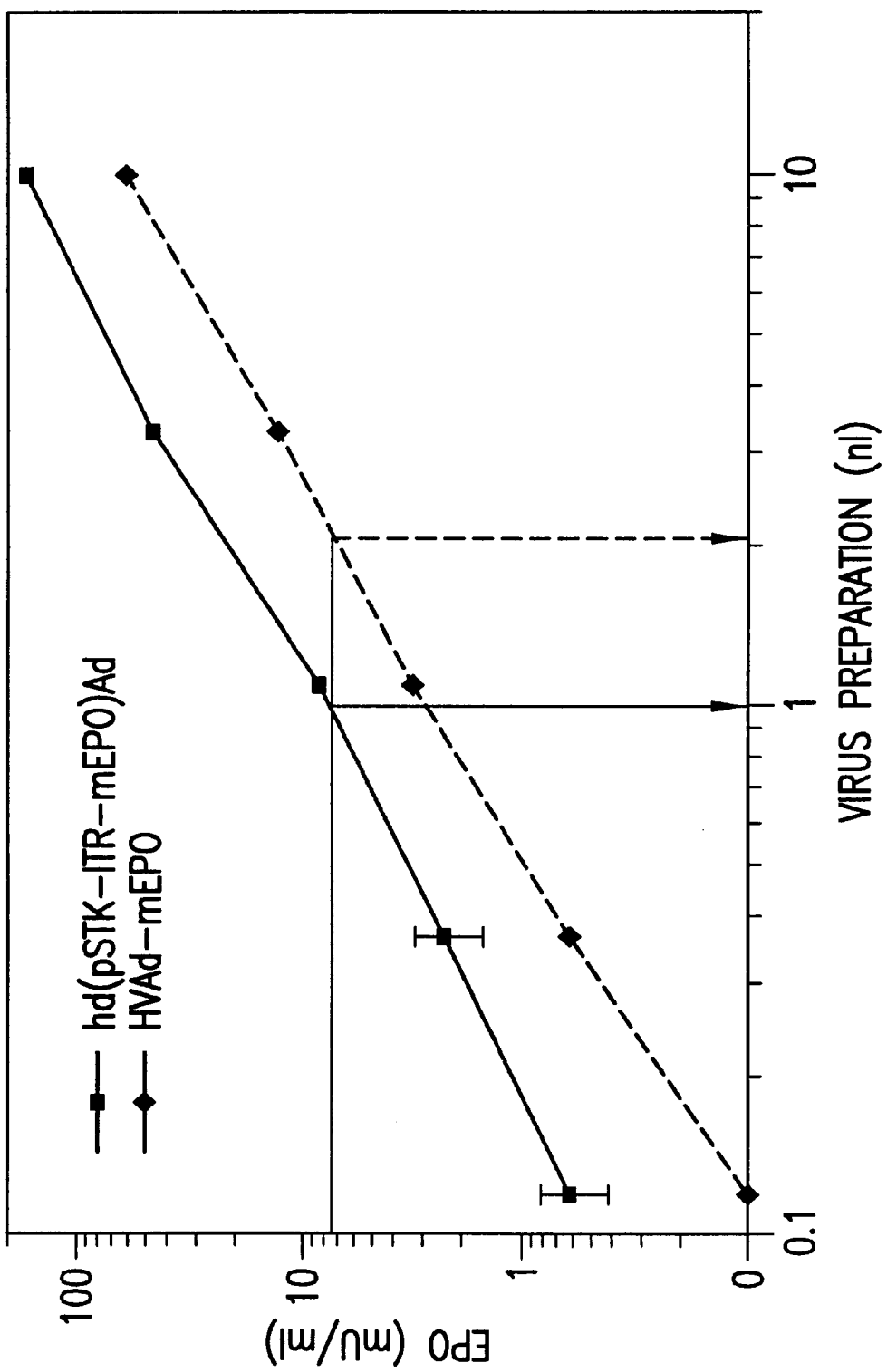
FIG. 2 shows a comparison of EPO levels produced in HeLa cells following infection with Hd-AV according to the invention or an adenovector encoding EPO (HV Ad-mEPO) generated according to Chartier et al. (1996). J. Virol. 70:4805–4810, indicating twice as many of the latter required to produce an equivalent level of EPO as with the relevant embodiment of the invention, the experiments being described in Example 4.

Vectors Expressing Mouse EPO (a) mEPO expression cassette

The mEPO cDNA (Shoemaker and Mitsock (1986). Mol. Cell. Biol. 6:849–858) was cloned by PCR with an overlapping set of synthetic oligonucleotides. An EPO expression cassette was constructed under the control of the EF1a promoter (Kim et al., 1990, Gene 91: 217–223).

(b) pSTK-ITR-mEPO

EPO expression cassettes were inserted between AAV-ITRs (which would allow for site-specific integration of the EPO encoding sequence if used in conjunction with Adeno-Associated Virus (AAV) Rep integrase), and this was cloned in a HD adeno vector, pST120 backbone, obtained from Dr. S. Kochanek, formerly at Baylor College, now University of Koln) (Schiedner et al., February 1998, Nature Genetics 18: 180–183; Morsy et al. (July 1998) PNAS USA 95: 7866–7871).

Results

The vector pSTK-ITR-mEPO was amplified in 293-cre cells and purified. The genomic structure of the packaged virus was characterised and was found to be homogeneous and not to have undergone any detectable rearrangement. Infection of cultured cells with this vector gave rise to elevated production of mEPO in vitro.

In vivo delivery of pSTK-ITR-mEPO was studied in BALB/c, in CD-1 and DBA/2J mice. Viral preparations were injected at different doses ranging from 0.1 $\mu$l to 250 $\mu$l (1 $\mu$l contains approximately $2 \times 10^9$ physical particles corresponding to approximately $2 \times 10^7$ transducing units). Both circulating EPO levels and haematocrit (HCT) increases were monitored.

Discussion

From the data collected, some conclusions can be drawn:

(1) EPO levels in the blood are stable for more than five months and a precise dose-response curve can be observed;

(2) Although at doses above 1 $\mu$l a saturating increase of HCT are obtained, doses of 1 $\mu$l and below lead to submaximal but stable HCT increases well within physiological ranges;

(3) The efficacy in vivo on a particle basis of the HD-Ad mEPO vector is far superior (1,000- to 10,000-fold) with respect to first generation Adenoviruses carrying mouse EPO reported in the literature.

In particular, the last result is surprising and totally unexpected.

The extraordinary higher in viva transduction efficiency of the HD-Ad mEPO, with respect to first generation Adenoviruses carrying mouse EPO reported in the literature, has the following advantages:

(a) low doses of virus are sufficient to achieve statistically significant biological effect;

(b) there is total absence of detectable immune response, which correlates with long lasting effect;

(c) it is possible to re-inject the virus and obtain again biological effect, consistent with the absence of any detectable neutralising antibodies after first injection.

EXAMPLE 1

Construction of hd(pSTK-ITR-mEPO)Ad: a Helper Dependent Ad/AAV Recombinant Vector Carrying the Mouse EPO Gene (a) mEPO expression cassette The cDNA coding for mouse EPO (mEPO) was assembled from synthetic oligonucleotides (Stemmer et al. (1995). Gene 164:49–53). Roughly 30 bp of the 5' untranslated region (UTR) upstream of the initiator ATG were also synthesised, because it has been shown that a construct containing such a region of the 5' UTR is able to direct synthesis of mEPO in COS cells (Shoemaker and Mitsock (1986). Mol. Cell. Biol. 6:849–858.). For cloning purposes, a PstI restriction site was added at the 5' end of the cDNA and a BamHI restriction site was added at the 3' end of the cDNA, both sites added by PCR technique.

The CDNA was cloned PstI-BamHI in pBluescript II and was verified by sequencing. In vitro transcription and translation was used to provide confirmation the vector encoded a protein of the expected size.

The bovine growth hormone poly A site was amplified by PCR from plasmid pcDNA3 (Invitrogen, nucleotides 983–71249) at the same time adding a NotI site at the 3' end for cloning purposes. The bovine growth hormone poly A site was cloned XbaI-NotI in pBluescript II, downstream of the mEPO cDNA.

A 1.2 kb DNA fragment, containing the enhancer/promoter of the human elongation factor 1α gene, was excised (with HindIII and EcoRI) from the expression cassette present in pEF-BOS (Mizushima and Nagata (1990). Nucl. Acids Res. 18:5322) and it was cloned HindIII-EcoRI in pBluescript II, upstream of the mEPO cDNA. The chosen regulatory element (which contains also an intron) is known to give in vivo expression levels higher than viral promoters like RSV-LTR of CMV and to be stable over time in immunocompetent animals (Guo et al. (1996). Gene Therapy 3:820–810).

The entire expression cassette is flanked by unique restriction sites (KpnI, SalI, ClaI and HindIII at the 5': NotI, BssHII, PvuII and PvuI at the 3') which allow easy excision from the plasmid and directional cloning in a gene therapy vector of interest. The expression cassette is compact, having a minimal size of only 2 Kb, which can be extended up to 5 Kb by inclusion of plasmid vector sequences.

The mEPO expression cassette was transfected in human 293 cells. While the mEPO cDNA directed the synthesis of a polypeptide of apparently 21 kDa by in vitro transcription/translation (in good agreement with an expected size of 24 kDa for a 192 aa polypeptide), in the supernatant of the transfected 293 cells an anti-hEPO monoclonal antibody (cross-reactive with mEPO), recognized a protein migrating with an apparent molecular weight of 37 kDa, in good agreement with the 34 kDa reported molecular weight for natural mEPO, which is due to post-translational modification (mEPO has 3 potential N-linked glycosilation sites). With an ELISA kit developed for hEPO, but which also recognises mEPO, it was determined that 14 hours post-transfection the levels of mEPO in the cell culture supernatants already exceeded 200 pg/ml, and at 40 hours post-transfection the mEPO levels were much higher (judging by Western blot analysis), totally out of scale in the ELISA assay.

(b) PSTK-ITR-mEPO plasmid

The mEPO expression cassette (mEPO cDNA flanked by the enhancer/promoter of the human Elongation factor 1α gene and by the bovine GH poly A signal) was inserted between AAV ITRs. The ITRs are the minimal signal sequence required for rescue, replication, packaging and integration of the AAV genome (Carter, B J. in "Handbook of Parvoviruses", ed. P. Tijsser, CRC Press, pp.155–168; WO96/36364). Targeting of integration involves the AAV rep gene products. In particular, the larger polypeptides Rep 78 and Rep 68 have been shown to bind in vitro the AAV ITRs and the aavsl, and possess helicase and site-specific endonuclease activities which may be required for AAV replication as well as AAV integration. See for example Shelling, A. N., et al. (1994). Gene Ther. 1, 165–169; Balague, C., et al. (1997). J. Virol. 71, 3299–3306; Surosky R. T., et al (1997) J. Virol. 71,7951–7959.

The entire construct was subcloned in the unique SmiI restriction site of the restriction-dependent hd adenoviral vector pSTK120, generating pSTK-ITR-mEPO. pSTK120 is a pBluescrptIIKS-based plasmid that contains (in the following order) the Ad5 inverted terminal repeat (ITR) sequence and the packaging signal ψ, 440 bp (nucleotides 1–440); a 16,054 bp stuffer fragment of hypoxantine guanine phosphoribosyltransferase (nucleotides 1,799–17,853 in gb:humhprtb); a HindIII 9,063-bp fragment of C346 cosmid (nucleotides 12,421–21,484 in gb:L31948); and the right-end terminus of Ad5, composed of the ITR sequence, 117 bp (nucleotides 35,818–35,935).

EXAMPLE 2

Production of hd(pSTK-ITR-mEPO)Ad: a hd Adenovirus Expressing

In order to follow the amplification of the hd lmEPO Ad virus, an infection assay was set up.

HeLa cells (which have no endogenous EPO background production) were seeded in 24-well plates and infected with cell lysates derived from 293cre cells amplifying the hd mEPO Ad virus. After two washes to remove the EPO produced by the 293cre cell, HeLa cells were cultured for 24 hours and EPO was detected in the supernatant with an ELISA kit.

EPO production was detected from HeLa cells infected with the passage 1 (P1) derived from 293cre transfected with pSTK-ITR-mEPO (after linearization with PmeI restriction which, by cleaving at the two PmeI flanking sites releases the linear pseudo-vital pro-genome and eliminates the pBluescriptII plasmid backbone) and infected with the helper virus AdLC8cluc.

EXAMPLE 3

Amplification and Characterization of hd(pSTK-ITR-mEPO)Ad

Two independent amplifications of the hd(pSTK-ITR-mEPO)Ad helper-dependent Adenovirus in 293cre4 cells were carried out. Aliquots of lysates from the various amplification passages were tested for induction of EPO production in the HeLa infection assay as described in Example 2, with the following results:

| Passage | Amplification A | | Amplification B | |
| --- | --- | --- | --- | --- |
| | EPO, mU/ml | Increase | EPO, mU/ml | Increase |
| P1 | 1.0 | 1 | 3.6 | 1 |
| P2 | 10.4 | 10 | 55.9 | 15 |
| P3 | 40.0 | 40 | 178.2 | 50 |
| P4 | 23.9 | 24 | 84.5 | 23 |
| P5 | 37.3 | 37 | 120.5 | 33 |
| P6 | 448.7 | 449 | 1695.0 | 470 |
| P7 | 4920.0 | 4920 | 11500.0 | 3194 |
| P8 | 44300.0 | 44300 | 43900.0 | 12195 |

The virus increase at any given passage can be easily obtained simply dividing the EPO levels at that passage by the EPO levels at passage 1.

Although there was lack of amplification at passages 4 and 5 in both experiments, at passage 8 there was an increase of at least 4 logs in the amount of virus-induced EPO production by infected HeLa cells.

The helper-dependent virus was prepared on large scale, and viral DNA was extracted from part of the preparation, and was restricted with 6 different enzymes, side by side with the original pSTK-ITR-mEPO plasmid. No rearrangement was detectable in the restriction pattern.

Aliquots of the hd(pSTK-ITR-mEPO)Ad adenovirus CsCl purified preparation (up to 10 μl in duplicate) were used in a plaque forming assay on 293 cells to measure helper virus contamination. Helper virus titre was measured as $3 \times 10^6$ pfu/ml.

The concentration of physical particles in the preparation was measured as $2 \times 10^{11}$/ml, therefore the titre of EPO transducing units might be close to $10^9$/ml. The titre of EPO transducing units was determined as described in Example 4.

EXAMPLE 4

Construction of HVAd-mEPO: a ΔE1 Ad Vector Carrying the Mouse EPO Gene and Its Use to Determine the Infectious Titer of hd(pSTK-ITR-mEPO)Ad A ΔE1 Ad vector containing the same mEPO expression cassette as in the illustrative embodiment of the present invention was generated according to Chartier et al., 1996, (HVad-mEPO) and its titre was measured as $1.3 \times 10^9$ pfu/ml by conventional plaque assay.

Different volumes of hd(pSTK-ITR-mEPO)Ad and of HVAd-mEPO virus preparations were used in the HeLa infection assay described in Example 2 and the concentration of EPO in the supernatants of the infected cells determined. The results are shown in FIG. 2.

The concentration of infectious units of the hd(pSTK-ITR-mEPO)Ad preparation is roughly 2-fold higher as compared to the concentration of infectious units of the HVAd-mEPO preparation. The titre of the HVAd-mEPO preparation was measured as $1.3 \times 10^9$ pfu/ml (by conventional plaque assay) so the titre of the hd(pSTK-ITR-mEPO) Ad preparation can be estimated as $2.6 \times 10^9$ pfu-Equivalent/ml (pfu-E/ml).

Considering that the concentration of physical particles titre of the hd(pSTK-ITR-mEPO)Ad preparation was measured as $2 \times 10^{11}$/ml (see previous example), the ratio pfu: physical particles can be estimated as roughly 1:100, in perfect agreement with what is known for ΔE1 Ad vectors (Barr and Kay (1997). Methods for delivery of Genes to hepatocytes in vivo using recombinant Adenovirus vectors. In Gene Therapy Protocols. P. D. Robbins. editor. Human Press, Totowa, N.J. 205–212).

Finally, considering that helper virus titre in the hd(pSTK-ITR-mEPO)Ad preparation was measured as $3'\times10^6$ pfu/ml (see previous example), the percentage of helper virus contamination can be estimated as roughly 0.1%, therefore 99.9% of infectious units in the hd(pSTK-ITR-mEPO)Ad preparation are helper-dependent viral particles.

In the following examples, the doses used in vivo are reported as pfu-E and not as volumes or physical particles.

EXAMPLE 5

In vivo Testing of hd(pSTK-ITR-mEPO)Ad in BALB/c Mice

To test efficiency of gene delivery in vivo, the following doses of hd(pSTK-ITR-mEPO)Ad were injected in the tail vein of 8-week old immunocompetent female BALB/c mice: $8\times10^8$ pfu-E, $1\times10^8$ pfu-E, $7\times10^7$ pfu-E, $3\times10^7$ pfu-E, $1\times10^7$ pfu-E, $3\times10^6$ pfu-E (groups of 5 mice for each dose). Control mice were injected in the tail vein with saline solution (PBS).

Serum mEPO levels and haematocrit were measured at various times after virus injection. The results are summarised in FIG. 4.

Figure 4A:
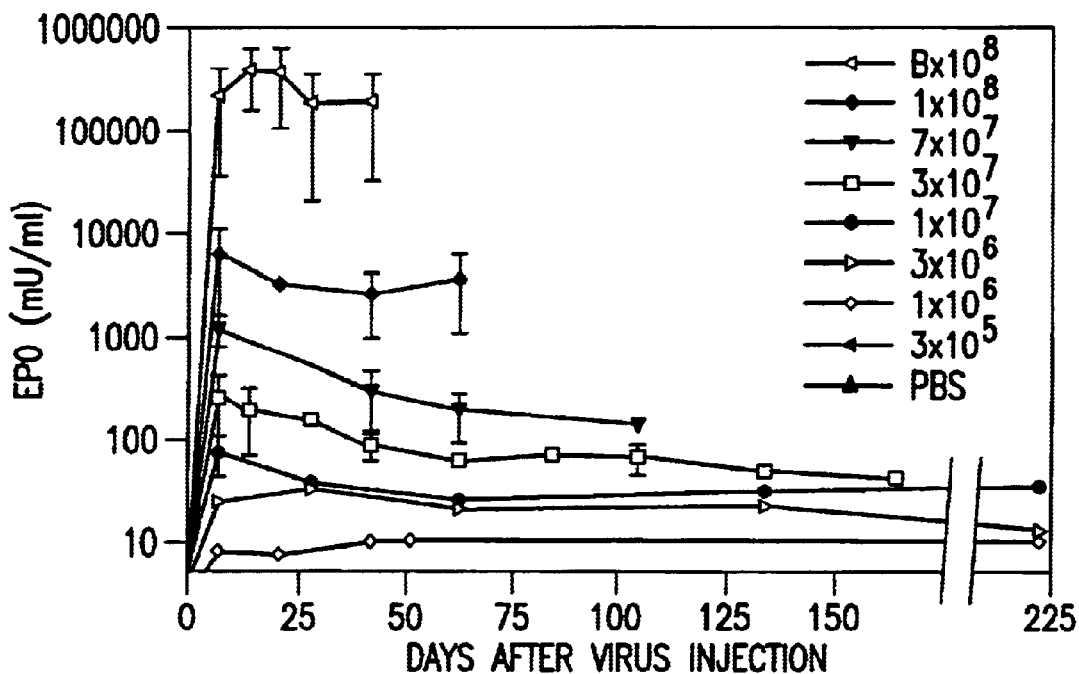
FIG. 4A shows mEPO levels (in mIU/ml). For mice injected with the $3\times10^5$ i.u. of virus and with PBS, the mEPO levels were below the 5 mIU/ml lower detection limit of the assay and are not shown in the figure.
Figure 4B:
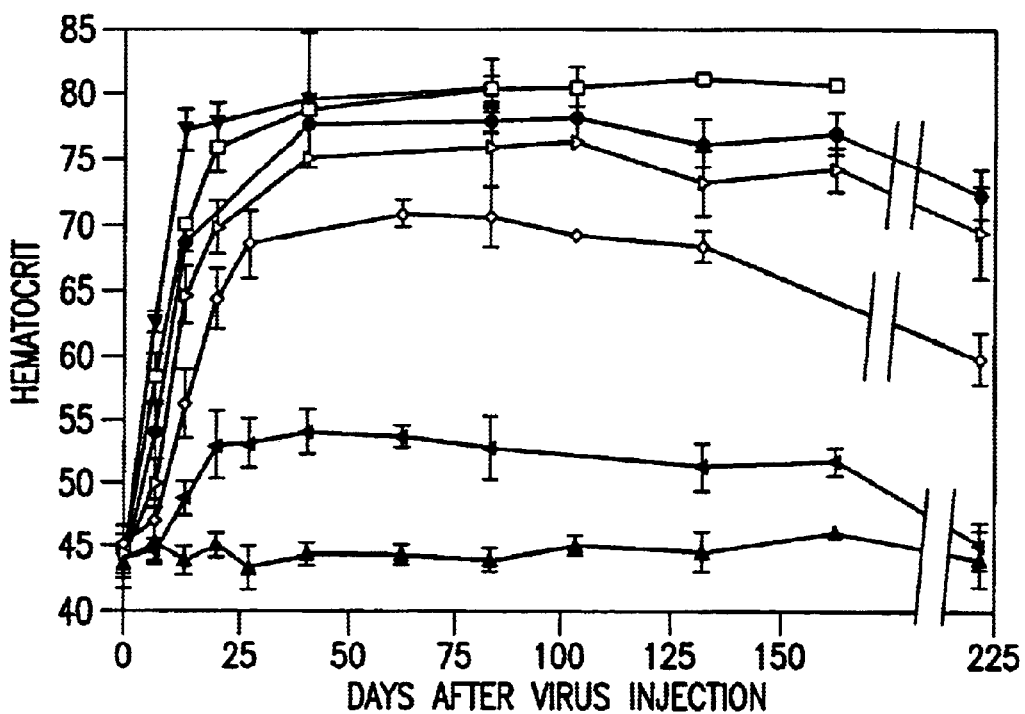
FIG. 4B shows haematocrit levels. The groups of mice injected with $8\times10^8$ and $1\times10^8$ i.u. had haematocrit levels similar to mice injected with $7\times10^7$ or $3\times10^7$ i.u. and are not shown for clarity of illustration.

FIG. 4 shows that there is an evident dose-response in the levels of serum EPO as a function of the viral dose injected, and EPO levels seem to be stable until day 105 after injection (this being the last time point at which mEPO detection was performed). Early deaths occurred in the high dose injected groups: all animals injected with $8\times10^8$ pfu-E died within 42 days after virus injection, all animals injected with $1\times10^8$ pfu-E died within 63 days after virus injection, all animals injected with $7\times10^7$ pfu-E died within 105 days after virus injection and 3 out of 5 animals injected with $8\times10^8$ pfu-E died within 140 days after virus injection. Autoptic analysis established that the causes of death were due to pronounced policitemia.

Three observations on haematocrit levels can be made from FIG. 4:
- (i) no dose-response could be observed at the higher doses tested ($8\times10^8$ pfu-E and $1\times10^8$ pfu-E, not shown; $7\times10^7$ pfu-E and $3\times10^7$pfu-E, FIG. 4). The lack of a dose dependence of the haematocrit levels may be due, at least in part, to the high level of EPO being produced which are already at a plateau above the levels giving a dose-response in the haematocrit.
- (ii) A dose-response could be observed at the lower doses ($1\times10^7$ pfu-E, $3\times10^6$ pfu-E), although haematocrit still reached high values (more than 75%) even at the $3\times10^6$ pfu-E dose.
- (iii) The haematocrit remains stable for at least 140 days after helper-dependent virus injection (duration of the experiment at the moment of writing).

To determine the minimal virus dose capable of giving an increase in haematocrit, a second group of BALB/c mice was injected with $1\times10^6$ pfu-E and $3\times10^5$ pfu-E virus doses. As vector dosage is decrease, a better dose-response in the rise of haematocrit levels is anticipated. The results are also summarised in FIG. 4.

FIG. 4 shows that mEPO is detectable in mice injected with the $1\times10^6$ pfu-E dose and it is stable for at least 85 days after helper-dependent virus injection (duration of the experiment at the moment of writing); mEPO is not detectable in mice injected with the $3\times10^5$ pfu-E dose (detection limit of the kit 5 mU/ml of mEPO), however FIG. 4 shows that these mice still show an increase in the haematocrit after virus injection, when compared to PBS-injected mice. It is of note that as little as $3\times10^5$ pfu-E ($1\times10^8$ physical particles) of virus (produced from as few as $10^4$ 293cre infected cells) are able to induce a statistically significant increase in haematocrit in the strongly immunocompetent BALB/c mice, increase which is stable for at least at day 84 after virus injection.

EXAMPLE 6 in vivo Testing of hd(pSTK-ITR-mEPO)Ad in DBA/2J Mice

To test efficiency of gene delivery in vivo, the following doses of hd(pSTK-ITR-mEPO)Ad were injected in the tail vein of 8-week old immunocompetent female DBA/2J mice: $1\times10^7$ pfu-E, $3\times10^6$ pfu-E, $1\times10^6$ pfu-E, $3\times10^5$ pfu-E (groups of 5 mice for each dose). Control mice were injected in the tail vein with saline solution (PBS).

Serum mEPO levels and haematocrit were measured at various times after virus injection. The results are summarised in FIG. 5.

Also in this immunocompetent strain a dose response to virus injection was observed for both circulating EPO levels and haematocrit increase. It is worth nothing that in this strain the vector expression and efficacy is apparently much higher than in BALB/c: the $3\times10^5$ pfu-E dose (lowest dose tested) gives quite detectable mEPO levels, between 20 and 30 mU/ml (mEPO was undetectable in age-matched BALB/c mice injected with the same dose of virus) and the haematocrit reached levels of 83.3% 42 days after injection. Indeed, all animals injected with the three higher doses already died due to complications related to pronounced polycitemia (some animals reached 91% hct just before death); only some animals injected with the $3\times10^5$ pfu-E dose are surviving (4 out of 6) and their haematocrit has been stable around 83% over the last 43 days.

Also in this mouse strain transgene expression by the helper-dependent adenoviral vector was stable for the entire duration of the experiment (84 days at the moment of writing).

EXAMPLE 7

In vivo Testing of hd(pSTK-ITR-mEPO)Ad in CD-1 Mice

To test efficiency of gene delivery in vivo, hd(pSTK-ITR-mEPO)Ad was injected in the tail vein of 8-week old immunocompetent CD-1 female mice at the following doses: $1\times10^7$ pfu-E, $3\times10^6$ pfu-E, $1\times10^6$ pfu-E, $3\times10^5$ pfu-E (groups of 6 mice for each dose). Control mice were injected fin the tail vein with saline solution (PBS).

Haematocrit was measured at various times after virus injection. The results are summarised in FIG. 5.

Again, also in this immunocompetent strain a dose response to virus injection was observed for haematocrit increase. It is worth nothing that in this strain the vector expression and efficacy is apparently higher than in BALB/c, but lower that in DBA/2J: the $3\times10^5$ pfu-E dose (lowest dose tested) gives haematocrit levels around 60%, therefore higher than the ones observed in age-matched BALB/c mice injected with the same dose of virus (53%), but lower than the ones observed in age-matched BALB/c mice injected with the same dose of virus (83%).

Therefore, as little as $3 \times 10^5$ pfu-E of virus (produced from as few as $10^4$ 293cre infected cells) are able to induce a very significant increase in haematocrit in all 3 immunocompetent mice strain tested, albeit with different efficacy (DBA/2J>CD-1>BALB/c).

EXAMPLE 8

Follow-up of Mice Injected with HD(pSTK-ITR-mEPO)Ad

Mice injected with virus hd(pSTK-ITR-mEPO)Ad (Examples 5, 6 and 7) were followed to assess the longevity of expression. The results for BALB/c mice (Examples 5) are shown in FIG. 4. All animals injected with doses equal to or higher than $3 \times 10^7$ pfu-E died due to complications related to the pronounced polycythemia. It is remarkable to notice that the haematocrit remained elevated for at least 225 days after HD(pSTK-ITR-mEPO)Ad injection at doses equal to or higher than $1 \times 10^6$ pfu-E.

Figure 5A:
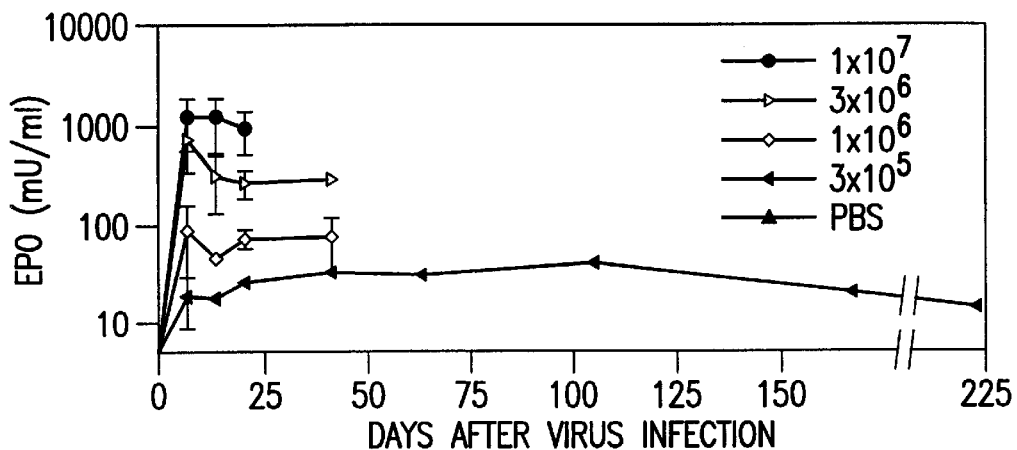
FIG. 5A shows mEPO levels.
Figure 5B:
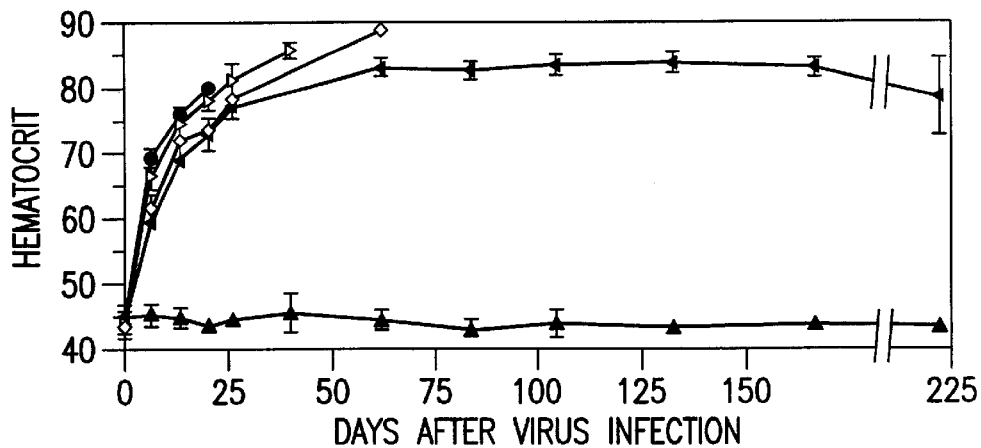
FIG. 5B shows haematocrit levels.

The results for DBA/2J mice (Example 6) are shown in FIGS. 5A and 5B. Again, in the group injected with $3 \times 10^5$ pfu-E of HD(pSTK-ITR-mEPO)Ad, elevated mEPO levels (FIG. 5A) and, consequently, elevated haematocrit levels (FIG. 5B) persisted for at least 225 days after the injection.

Figure 5C:
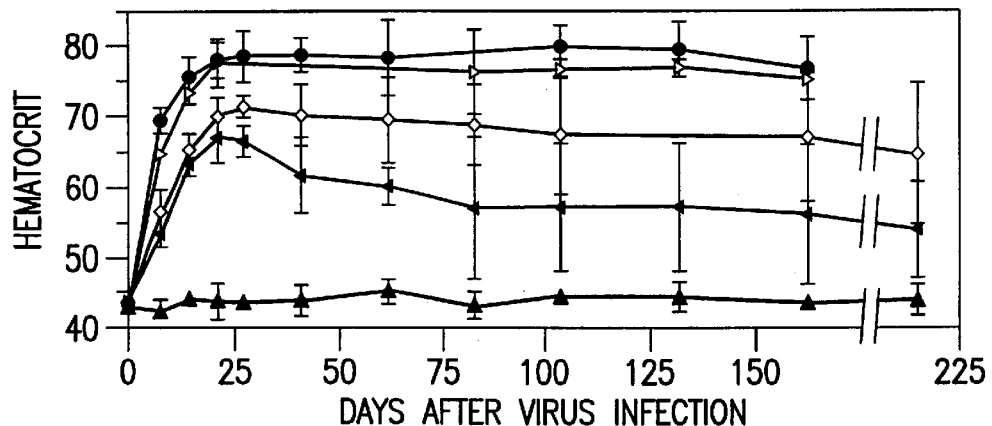
FIG. 5C shows results of experiments in which groups of healthy adult female CD-1 mice (n=9) were infused in the tail vein with the same doses of hd(pSTK-ITR-mEPO)Ad virus: haematocrit levels are shown.

The results for CD-1 mice (Example 7) are shown in FIG. 5C. In this mice also the haematocrit remained elevated in all groups for at least 220 days after the HD(pSTK-ITR-mEPO)Ad virus injection.

EXAMPLE 9

Induction of Neutralizing Antibodies Against Injected Viruses

Humoral immune responses, in particular the induction of neutralizing antibodies against capsid proteins (Tripathy et al, (1996) Nature Med 2, 545–550 ), are a fundamental problem in animals injected with E1-deleted adenoviruses (Mastrangeli et al. (1996) Hum Gene Ther 7, 79–87) because they can limit further re-administration of the same or of a different adeno vector.

Formation of neutralising antibodies against hd(pSTK-ITR-mEPO)Ad and HVAd-mEPO was studied in BALB/c mice. Neutralising antibody assays were performed as described by Jooss et al. Gene Ther 5:309, 1998, with minor modifications. Briefly, after 1 h preincubation of $2 \times 10^4$ i.u. of HD(pSTK-ITR-mEPO)Ad with serial dilutions of heat-inactivated serum [from HD(pSTK-ITR-mEPO)Ad or HVAd-mEPO injected mice] in DMEM (Gibco) plus 0.2% foetal bovine serum (50 µl, starting 1:10), the virus was applied onto $10^5$ HeLa cells in 96-well plates. Following 1 h infection, the inoculum was sucked and 250 µl of fresh DMEM (Gibco) plus 10% foetal bovine serum (Gibco) were added. After 24 h medium was harvested and mEPO concentration was measured using the Quantikine IVD rhEPO ELISA kit (R&D System, Minneapolis, Minn.) following the instruction furnished by the manufacturer. The neutralizing antibody titer was defined as the dilution of serum which lead to a 50% reduction of mEPO levels in the cell culture supernatants compared to HeLa cells infected with virus incubated with serum from naive mice.

Injection of $1.2 \times 10^8$ physical particles (p.p.) of the two viruses did not significantly induce the formation of neutralizing antibodies whereas, again in both cases, higher virus doses induced neutralizing antibodies (see table below). It is important to notice that neutralizing antibody titers were not significantly induced upon injection of both the first generation and the HD vectors at doses low ($1.2 \times 10^8$ p.p., corresponding to $3 \times 10^6$ pfu and $1.2 \times 10^6$ i.u., respectively), but still able to induce haematocrit elevation (FIG. 3).

Formation of Neutralising Antibodies After hd and First Generation Virus Injection

| Virus | Physical particles | Titre |
|---|---|---|
| 1st generation HVAd-mEPO | $1.2 \times 10^8$ | <10 |
|  | $1.2 \times 10^9$ | 47 |
|  | $1.2 \times 10^{10}$ | 130 |
| Helper Dependent hd(pSTK-ITR-mEPO)Ad | $1.2 \times 10^8$ | <10 |
|  | $1.2 \times 10^9$ | 37 |
|  | $1.2 \times 10^{10}$ | 180 |
| PBS | 0 | <10 |

Healthy adult female BALB/c mice were infused in the tail vein with various doses of HD(pSTK-ITR-mEPO)Ad or HVAd-mEPO, sera were harvested 35 days after virus injection and tested for neutralizing antibodies. Serial serum sera were incubated with $2 \times 10^4$ i.u. of HD(pSTK-ITR-mEPO)Ad for 1 hr and were then added $10^5$ HeLa cells. The antibody titers are the dilutions of serum which lead to a 50% reduction of mEPO levels in the cell culture supernatants compared to HeLa cells infected with virus incubated with serum from naive mice. The lowest dilution tested was 1:10.

EXAMPLE 10

Readministration of hd(pSTK-ITR-mEPO)Ad in BALB/c Mice

The feasibility of readministration of hd(pSTK-ITR-mEPO)Ad was tested in BALB/c mice, those which in the inventors' hands had been the most difficult to be transduced (Examples 5, 6 and 7).

Two groups of 8-week old female BALB/c-mice were injected in the tail vein with $3 \times 10^5$ pfu-E of hd(pSTK-ITR-mEPO)Ad virus (control mice were injected in the tail vein with PBS solution) and haematocrit was measured at various time after virus administration. The results of the experiment are summarized in FIG. 6.

Figure 6:
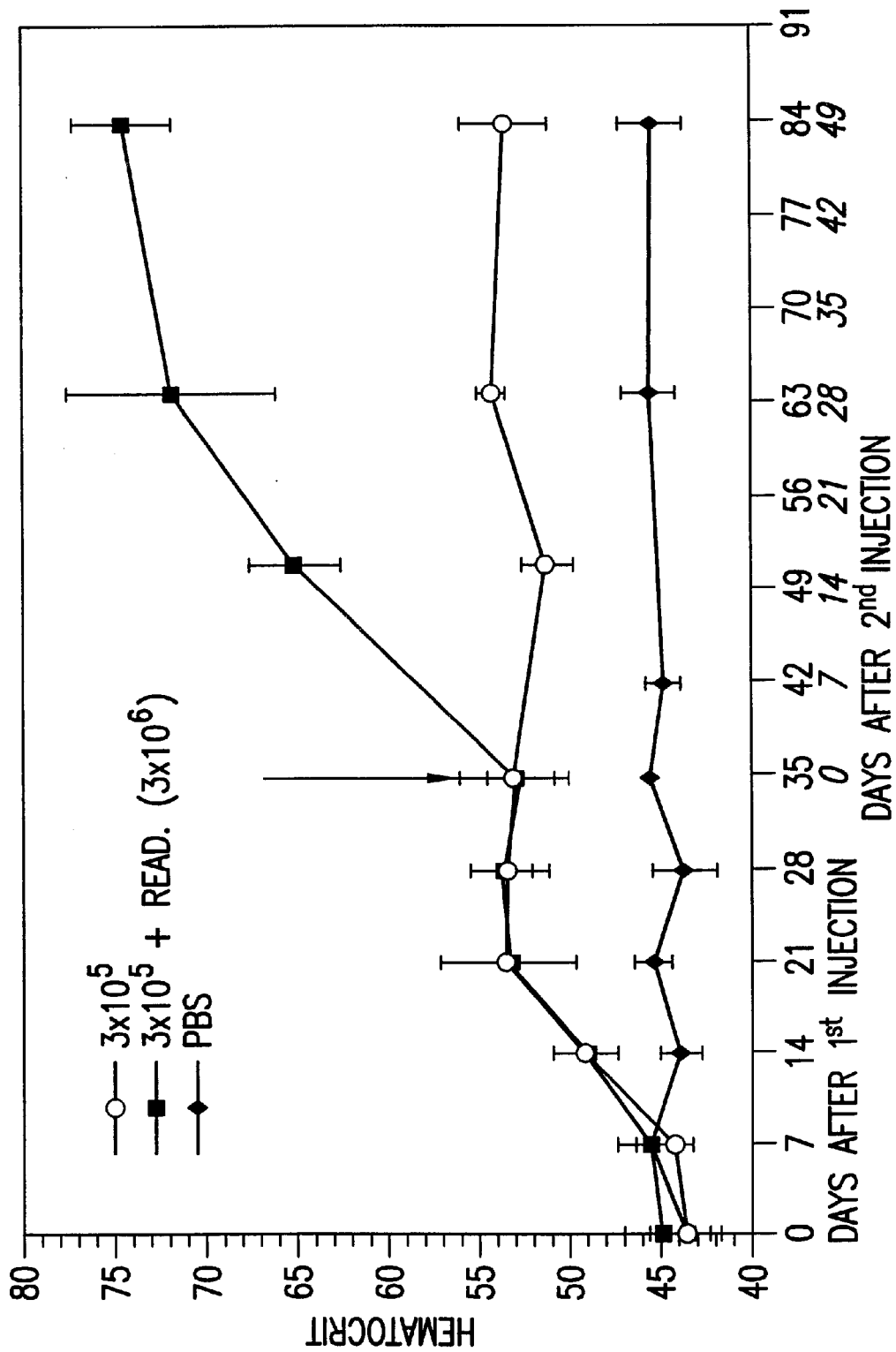
FIG. 6 shows haematocrit measurements in Balb/c mice at various days following first and second injections of Hd-AV according to the invention, as described in Example 10.

As a result of virus administration, haematocrit increased in the first 3 weeks after injection, to stabilize at levels around 53%. At day 35, after the haematocrit had stabilized, the group of mice whose mean haematocrit is indicated in FIG. 6 with a filled square was re-injected in the tail vein with $3 \times 10^6$ pfu-E of hd(pSTK-ITR-mEPO)Ad virus (injection indicated by an arrow in FIG. 6).

Surprisingly, the haematocrit of re-injected mice started increasing again to reach values well above 70% 49 days after the second injection, whereas the haematocrit of mice which did not receive the second injection remained stable at levels around 53% for the entire duration of the experiment (84 days at the moment of writing)

These results show that hd(pSTK-ITR-mEPO)Ad virus can be very successfully re-administered even at short times after the first injection, when the biological effects of the first injection are still present.

EXAMPLE 11

Long Term Re-administration of hd(pSTK-ITR-mEPO)Ad Virus

Figure 7A:
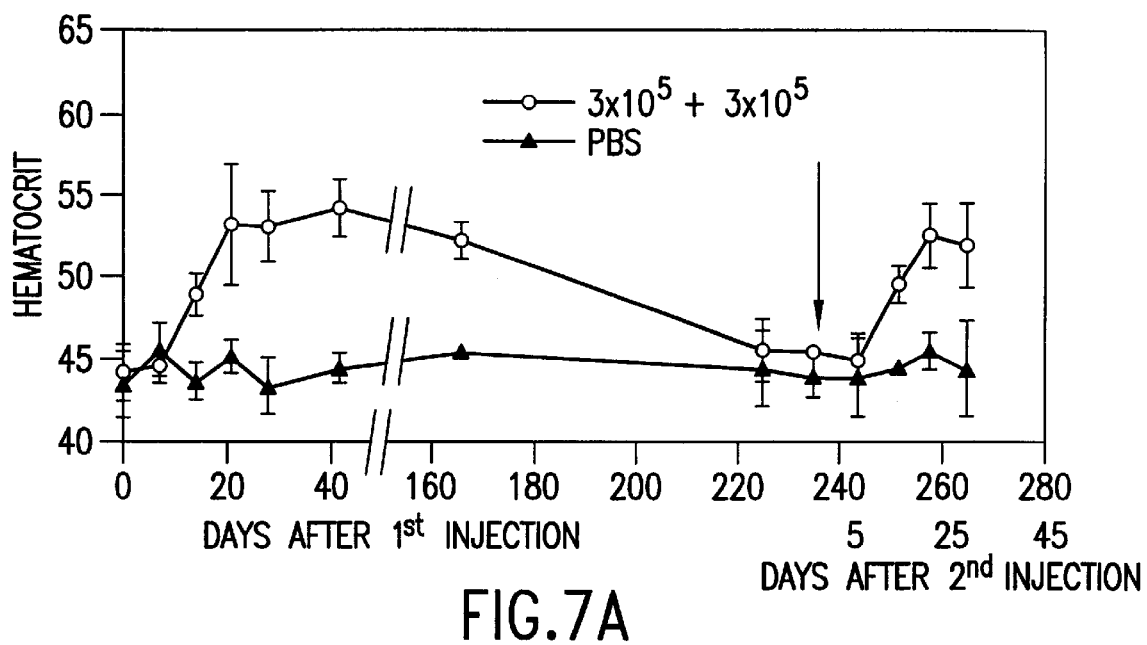
FIG. 7A shows results of experiments in which the same mice used in the experiments of which results are shown in FIG. 4, which received $3\times10$ i.u. of hd(pSTK-ITR-mEPO) Ad at time 0, were reinjected with a second dose of $3\times10^5$ i.u. (indicated by the arrow) 235 days after the first injection. Haematocrit levels are shown.

After the effects of the first hd-mEPO injection vanished (BALB/c) or were strongly reduced (in a subset of CD-1) it was possible to test efficiency of re-administration using also the same virus dose delivered with the first injection. Roughly 34 weeks p.i., BALB/c mice were infused again with $3 \times 10^5$ t.u of hd(pSTK-ITR-mEPO)Ad. Haematocrit rose to 52.5% 22 days after the second injection and then stabilised at the same levels observed after the first injection (FIG. 7A). The kinetics of haematocrit increase after the first and the second injection were identical (FIG. 7A). Virus-injected CD-1 mice show more individual variability as compared with the other strains, probably due to their outbred nature (FIG. 5C).

Figure 7B:
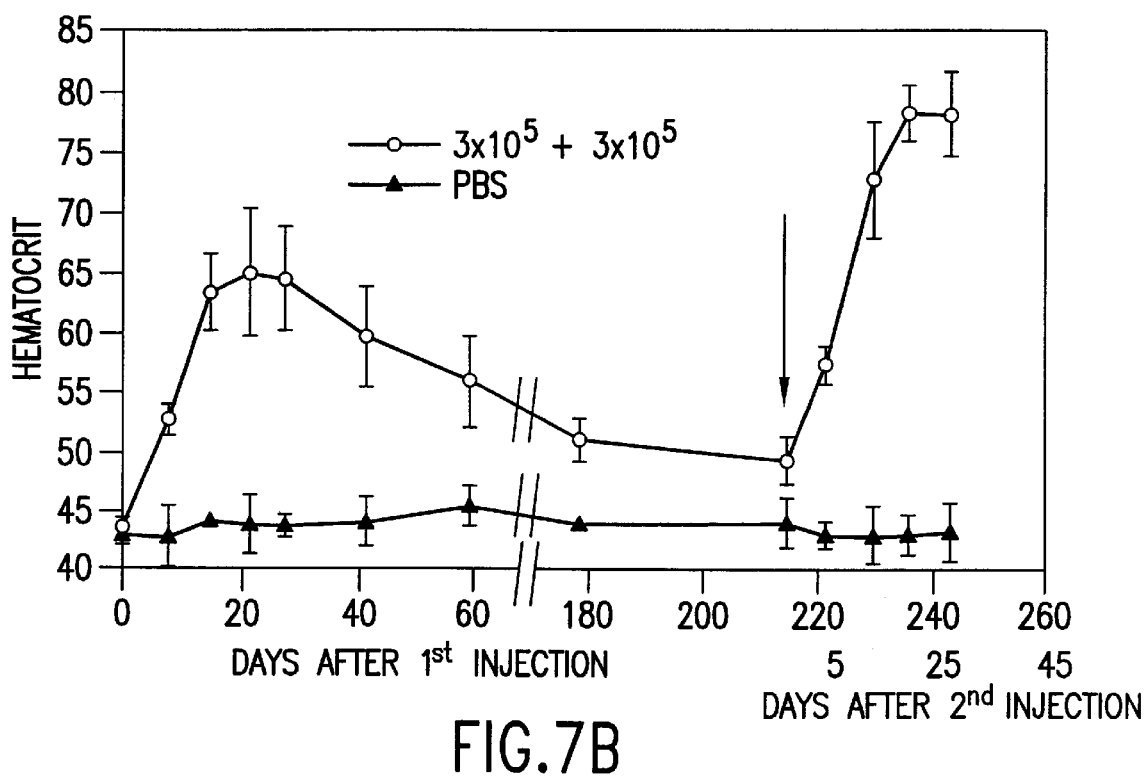
FIG. 7B shows results of experiments in which a subset of the mice used in the experiments of which results are shown in FIG. 5, which received $3'10^5$ i.u. of hd(pSTK-ITR-mEPO)Ad at time 0, were reinjected with a second dose of $3\times10^5$ i.u. (indicated by the arrow) 215 days after the first injection aematocrit levels are shown.

Within the group of mice injected with $3 \times 10^5$ i.u. of hd(pSTK-ITR-mEPO)Ad (FIG. 5C), the four mice with the lowest haematocrit were chosen. In this selected group the haematocrit reached 65% at 22 p.i. and slowly decreased to an average of 49.5% at 215 days p.i. (FIG. 7B). These mice were injected with a second dose of $3 \times 10^5$ i.u. of hd(pSTK-ITR-mEPO)Ad. Haematocrit rose abruptly to reach values of 78.5% 22 days after the second virus infusion, stabilizing at these high levels thereafter (FIG. 7B).

Therefore, re-administration of the same HD virus dose used for the first injection brought the haematocrit to that same levels observed after the first administration in the case of BALB/c mice, and to levels even higher in the case of CD-1 mice, probably due to accumulation with the residual HD vector from the first administration (average haematocrit was still 49.5±2% vs 44±2.1% of the controls at the time of reinjection). The haematocrit levels reached after re-administration strongly suggest that efficiency of reinjection is close to 100% even using a HD virus dose identical to the one used for the first injection. The fact that the HD virus allows both dose-escalation and long term readministration makes it unique among viral vectors.

EXAMPLE 12

In vivo Testing of hd(pSTK-ITR-mEPO)Ad in Sprague-Dowley Rats

The hd(pSTK-ITR-mEPO)Ad virus was injected into rats to assess not the duration of gene expression (problems may arise due to the rat immune response against the heterologous mouse EPO transgene), but the efficacy of transduction. This assessment was by measuring mEPO levels a short time after virus injection, before an eventual immune reponse against mEPO has the time to develop.

Doses of $2 \times 10^8$, $2 \times 10^7$ and $2 \times 10^6$ pfu-E were injected in the caudal vein, and mEPO and Hct levels were monitored at various times after virus administration. The results were as follows:

Also in this animal species, a nice dose-response to virus injection was observed both for hct increase and circulating mEPO levels in the first 27 days after administration.

Interestingly, in order to obtain circulating EPO levels around 10 mU/ml (therapeutically effective dose to correct anemia of Chronic Renal Failure) it was necessary to inject only $3 \times 10^5$ pfu-E in mice (CD-1) and $2 \times 10^6$ pfu-E in rats (Sprague-Dowley), corresponding to a dose of as little as $1 \times 10^4$ pfu-E/gram of body weight in both species.

Since the major current clinical indication for rEPO is anaemia of CRF (Paganini and Miller, (1993) Adv Intern Med 38, 223–243), hd(pSTK-ITR-mEPO)Ad virus injection was tested for treatment of anaemia of CRF, which develops in subtotally nephrectomized rats (Krumwieh et al. (1988) Behring Inst Mitt 83, 193–201).

Subtotal nephrectomy was performed in a group of Sprague Dowley rats. Female Sprague-Dowley rats anesthesized with kethamine-xylazine were used in this study. A longitudinal incision from the sternum to the lower part of the hypogastrium was performed. The right kidney was totally removed and two out of three branches of the renal artery of the left kidney were ligated with a silk thread. As a result, 70–75% of the left kidney became ischemic, leaving the animal with 12.5–15% of its original kidney mass functional. In response to kidney surgery the rats became uremic [Blood Urea Nitrogen (BUN) and creatinine levels were quantified using Spotchen Kidney 2 strips (Menarini Diagnostics, Florence Italy) for profile of renal funtion, the Auto Dry Chemistry Analyzer SPOTCHEM SP-4410 was used for strip analysis].

Figure 8A:
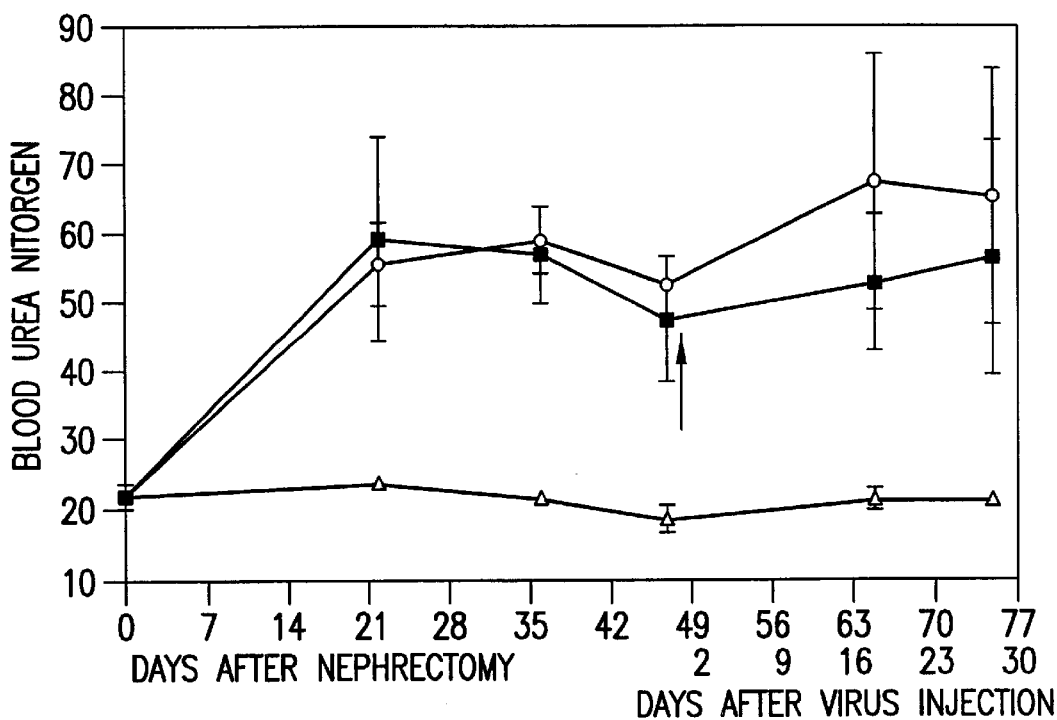
FIG. 8A shows Blood Urea Nitrogen (BUN) levels.
Figure 8B:
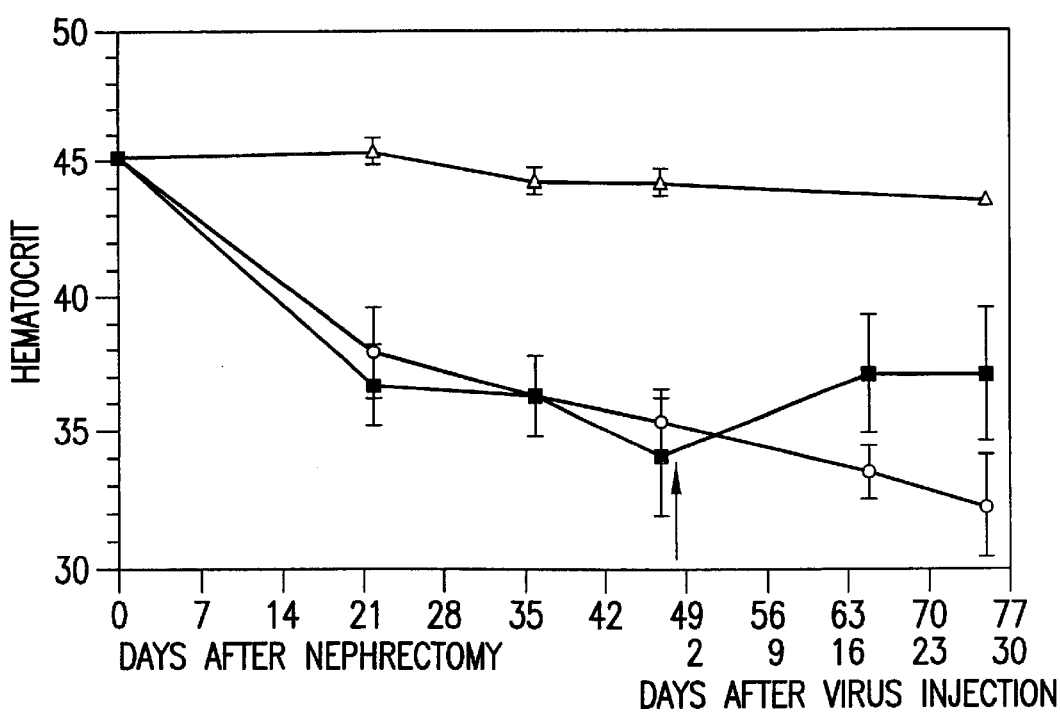
FIG. 8B shows haematocrit levels. Empty triangles: control rats. Empty circles: subtotally nephrectomized rats, injected i.v. with PBS 47 days after the surgery. Filled squares: subtotally nephrectomized rats, injected i.v. with hd(pSTK-ITR-mEPO)Ad ($3\times10^6$ i.u.) 47 days after the surgery. Arrows indicate virus or PBS injections.

Both plasma urea (FIG. 8A) and creatinine levels increased in operated animals as compared to controls. Haematocrit significantly decreased in partially nephrectomized animals, reaching levels around 35% roughly. 6½ week after surgery (FIG. 8B).

A single dose of $4 \times 10^6$ pfu-E of hd(pSTK-ITR-mEPO)Ad virus was injected i.v. in in a group of partially nephrectomized rats 47 days after the subtotal nephrectomy. The weight of the animals at the time of injection was roughy 400 grams, therefore the dose administered was of $10^4$ pfu-E/gram of body weight. Virus injection did not correct the status of uremia, as the plasma urea level of virus injected rats were not significantly different from those of uninjected rats (FIG. 8A). Interestingly, while subtotally nephrectomized uninjected rats showed deteriorating. anaemia, haematocrit increased after injection in subtotally nephrectomized virus-treated rats, reaching an average of 37.5% 28 days p.i. (FIG. 8B).

EXAMPLE 13

Construction of hd Virus Expressing Rat EPO and Use in Treatment of Nephrectomized Rats Preceding Examples report successful treatment of healthy or partially nephrectomized rats with the HD(pSTK-

| Virus dose | Days after virus injection | | | | | |
|---|---|---|---|---|---|---|
| | 0 days | | 13 days | | 27 days | |
| (pfu-E) | mEPO | Hct | mEPO | Hct | mEPO | Hct |
| $2 \times 10^8$ | <5 | 42 ± 1.4 | 767 ± 287 | 69.1 ± 2 | 324.6 ± 222.7 | 75.1 ± 4 |
| $2 \times 10^7$ | <5 | 42.1 ± 3 | 44.7 ± 19.1 | 64.1 ± 3.8 | 68.6 ± 53.8 | 71.7 ± 1.8 |
| $2 \times 10^6$ | <5 | 41 ± 1.7 | 14.5 | 50.6 ± 1.7 | 9.0 | 56.6 ± 4.3 |
| Control | <5 | 42.2 ± 1.9 | <5 | 45.5 ± 0.8 | <5 | 46.1 ± 0.3 |

ITR-mEPO)Ad virus. However, in both cases anti-mEPO antibodies started appearing at day 42, preventing long-term effectiveness of the treatment. Rat EPO differs from mEPO at 10 amino acids, clustered in three regions in the sequence.

DNA fragments containing the rat EPO-specific codons were amplified by PCR and joined to assemble a complete rat EPO cDNA, verified by sequence analysis. The rat EPO cDNA was inserted in the same expression cassette used for mEPO cDNA (expression driven by the EF1α promoter, bovine growth hormone polyadenylation signal at the 3'), and the entire expression cassette has been cloned in pSTK-120. The virus was amplified and amplification has been verified in the HeLa infection assay described in Example 2 up to passage 8. The virus was prepared on large scale and its genomic structure was verified by restriction with 2 different restriction enzymes: no rearrangement was detected.

Parallel infection assays were performed with the STK-ratEPO virus and with a ΔE1 Ad vector (whose titer has been determined by plaque assay) in which the mEPO cDNA is under the control of the same EF-1α promoter (FIG. 1), as described in Example 1. Supernatants of infected cells were analysed by western blotting using a mAb which is directed against the first 26 residues of the the protein (the first 26 residues of mouse and rat Epo are identical). Tests of EPO production performed in such a way allowed estimation of the titer of STK-ratEPO virus as $4 \times 10^9$ pfu-Equivalents/ml. Correction of Anaemia of CRF by hd(ratEPO)

Partial nephrectomy (total nephrectomy of one kidney, ⅔ kidney inactivation by artery ligation of the contralateral organ) was performed on Sprague Dowley rats as described above. The parameters of two animals randomly chosen as examples are shown in the following table. Also in this case, surgery induced anemia and uremia, although at a lower extent as compared with the previous experiment (compare the haematocrit and BUN data shown in the following table with FIG. 8).

| Days after nephrectomy | 37 | 62 | 98 | 111 | 136 |
|---|---|---|---|---|---|
| Days after 1st injection (STK-ratEPO 4 × 10e6 pfu-E) | | 0 | 36 | 49 | 74 |
| Days after 2nd injection (STK-ratEPO 4 × 10e7 pfu-E) | | | | 0 | 13 | 38 |
| Virus Injected | | | | | |
| Hematocrit | 34.5 | 39 | 42 | 43 | 50.5 |
| BUN (mg/ml) | 32 | 30 | 30 | 33 | 38 |
| Weight | 396 | 540 | | | |
| Control | | | | | |
| Hematocrit | 37.5 | 39 | 40.5 | 39 | 37.5 |
| BUN (mg/ml) | 32 | 29 | 31 | 30 | 34 |
| Weight | 450 | | | | |

Injection of $4 \times 10^6$ pfu-E ($7.4 \times 10^3$ pfu/kg) of hd(ratEPO) 9 weeks after surgery caused only a minor haematocrit increase, in agreement with the previous observation the a dose of $1 \times 10^4$ pfu-E/gram of body weight was necessary to induce a significant haematocrit increase. It was determined as described above that no anti Adeno neutralizing Abs were detected after the first injection. A second injection of $4 \times 10^7$ pfu-E ($7.4 \times 10^4$ pfu/kg) was performed 5 weeks after the first. Roughly 5 weeks after the second injection haematocrit increased of 13 points.

Thus, hd(ratEPO) injection can correct anemia induced by partial nephrectomy. The biological effect persisted for at least 10 week from the first injection. Furthermore, the virus can be readministered i.v. also in rats, consistently with what has been shown in mice.

EXAMPLE 14

Comparison of hd(pSTK-ITR-mEPO)Ad with a First Generation Virus Delivered by Intra-muscle Injection A number of studies have been published by other laboratories using first generation Adeno vectors carrying the EPO gene, indicating the limitations of such vectors in providing appropriate gene dosage.

For example, mouse EPO cDNA was delivered using a first generation Adeno vector (AdmEPO) injected in muscle by Svensson et al. (1997).

Figure 9:
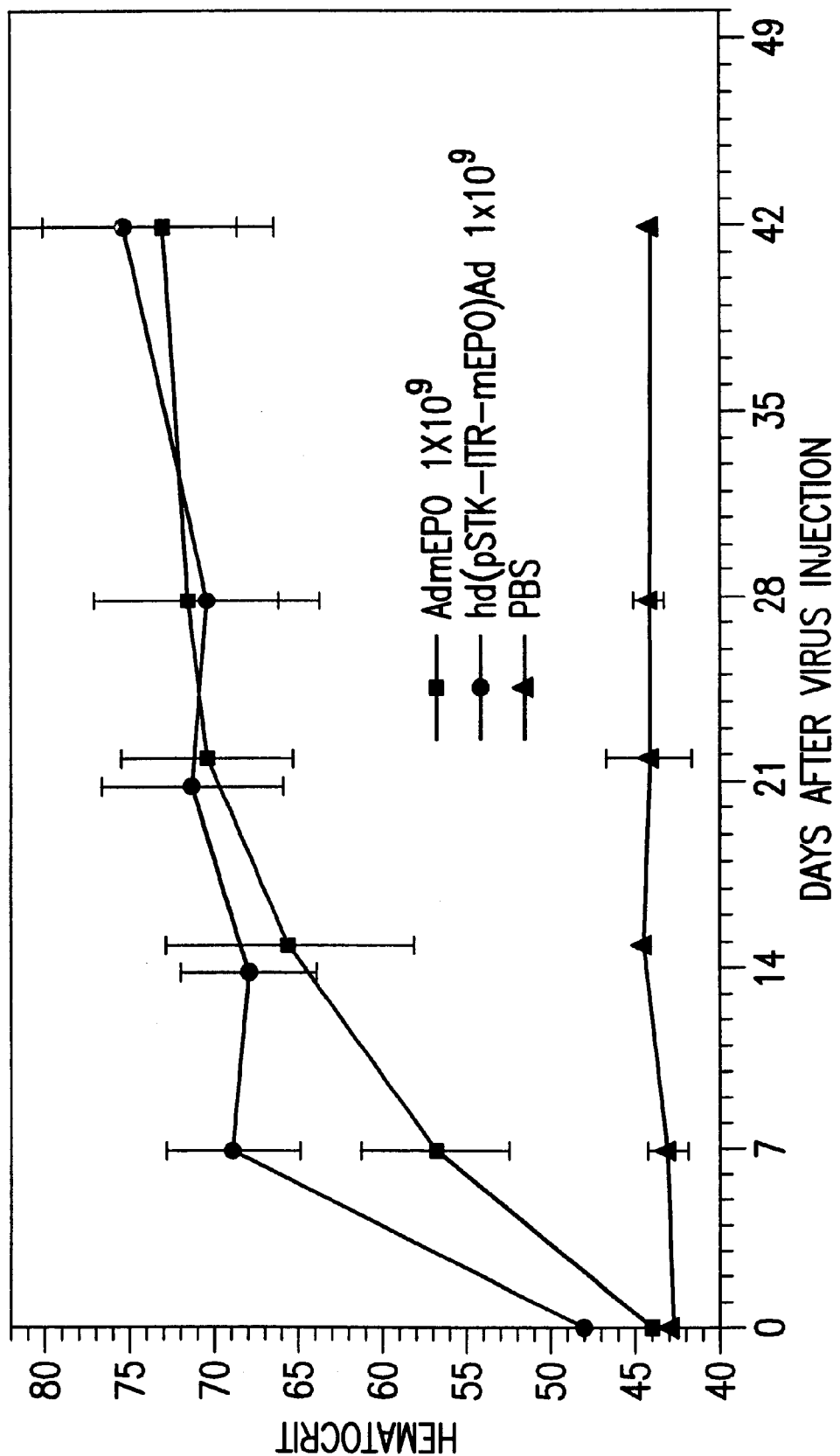
FIG. 9 shows haematocrit measurements in CD-1 mice at various days following injection of Hd-AV according to the invention or the adenovector encoding EPO (AdmEPO) of Svensson et al. (1997), indicating a much higher pfu (1000-fold greater) required for the adenovector to achieve a haematocrit increase comparable with that achieved using the present invention, the relevant experiments being described in Example 14.

FIG. 9 shows that $10^5$ pfu of first generation Adeno vector AdmEPO (data are derived from FIG. 1A in Svensson et al., 1997) are necessary to induce in CD-1 mice the same haematocrit increase induced by the injection of $10^6$ pfu-E of hd(pSTK-ITR-mEPO)Ad virus.

This indicates that hd(pSTK-ITR-mEPO)Ad virus is roughly 1,000-fold more potent than this particular first generation Adeno vector injected intramuscle in inducing haematocrit increase in immunocompetent CD-1 mice. In agreement with this conclusion, Svensson et al., 1997, states that "there is a treshold dose of virus ($2.5-8 \times 10^7$ pfu/gram of body weight) which is required to obtain long-term Epo expression and polycytemia ...". Example 12 above shows that such a threshold for hd(pSTK-ITR-mEPO)Ad virus is $1 \times 10^4$ pfu-E/gram of body weight (2,500–8,000-fold less).

EXAMPLE 15

Comparison of hd(pSTK-ITR-mEPO)Ad with a First Generation Virus Delivered by Intravenous Injection EPO cDNA was also delivered using a first generation Adeno vector (Ad.RSVepo) injected intravenously by Descamp et al. (1994).

Figure 10:
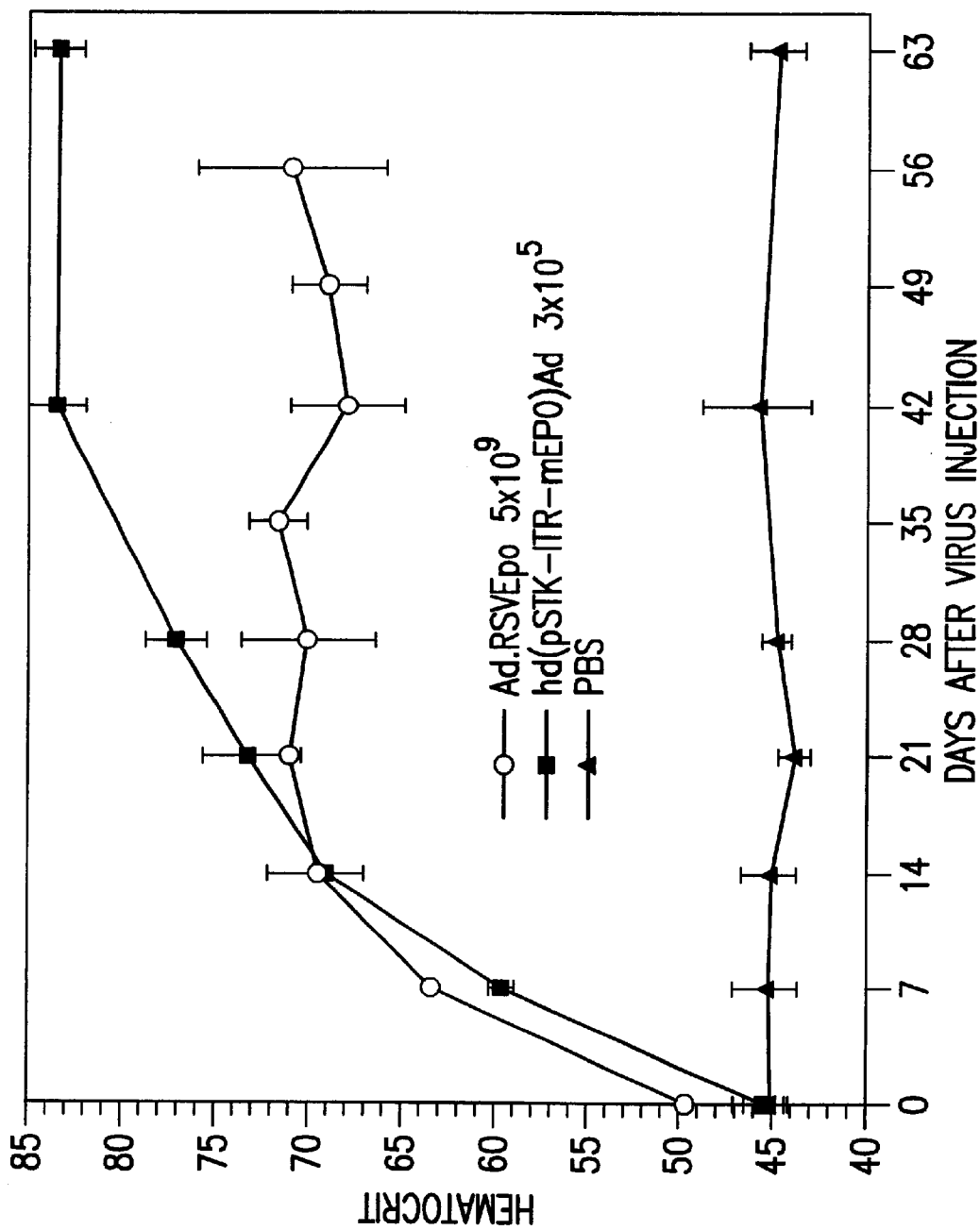
FIG. 10 shows haematocrit measurements in DBA/2J mice at various days following injection of Hd-AV according to the invention or the adenovector encoding EPO (Ad.RSVEpo) of Descamp et al. (1994), indicating a potency for the relevant embodiment of the present invention of roughly 10,000-fold greater, as described in Example 15.

FIG. 10. shows that $5 \times 10^9$ pfu of Ad.RSVepo injected intravenously (data are derived from Table 1 in Descamp et al., 1994) are not even sufficient to induce in DBA/2J mice the same haematocrit increase induced by the injection of $3 \times 10^5$ pfu-E (the lowest dose tested) of hd(pSTK-ITR-mEPO)Ad virus.

This indicates that hd(pSTK-ITR-mEPO)Ad virus is roughly 10,000-fold more potent than this particular first generation Adeno vector injected intravenously in inducing haematocrit increase in immunocompetent DBA/2J mice.

Therefore, the efficacy in vivo on a particle basis of the hd(pSTK-ITR-mEPO)Ad virus vector is far superior (1000- to 10,000-fold) to first generation Adenoviruses carrying mouse EPO reported in the literature.

In a further experiment, the efficiency of in vivo gene transfer of HD-mEPO and of Ad-mEPO was compared by injecting the two viruses i.v. in the tail vein of BALB/c mice.

Figure 3B:
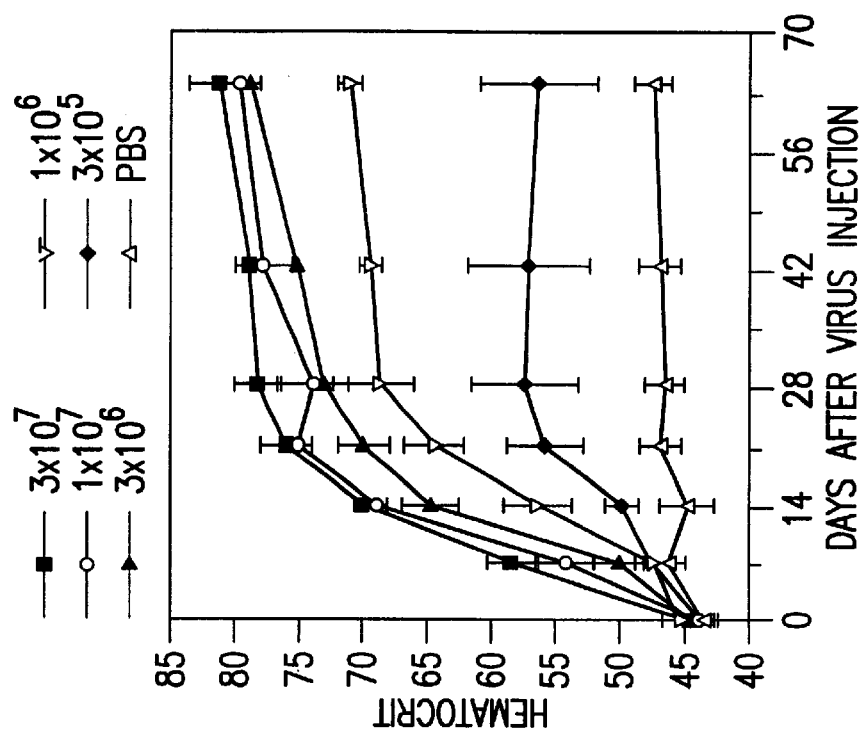
FIG. 3B shows results of experiments in which hd(pSTK-ITR-mEPO)Ad was injected at the same doses and two other mice groups, injected with doses of $3\times10^5$ and $1\times10^6$ i.u. (n=5 each), were also included in the experiment.
Figure 3A:
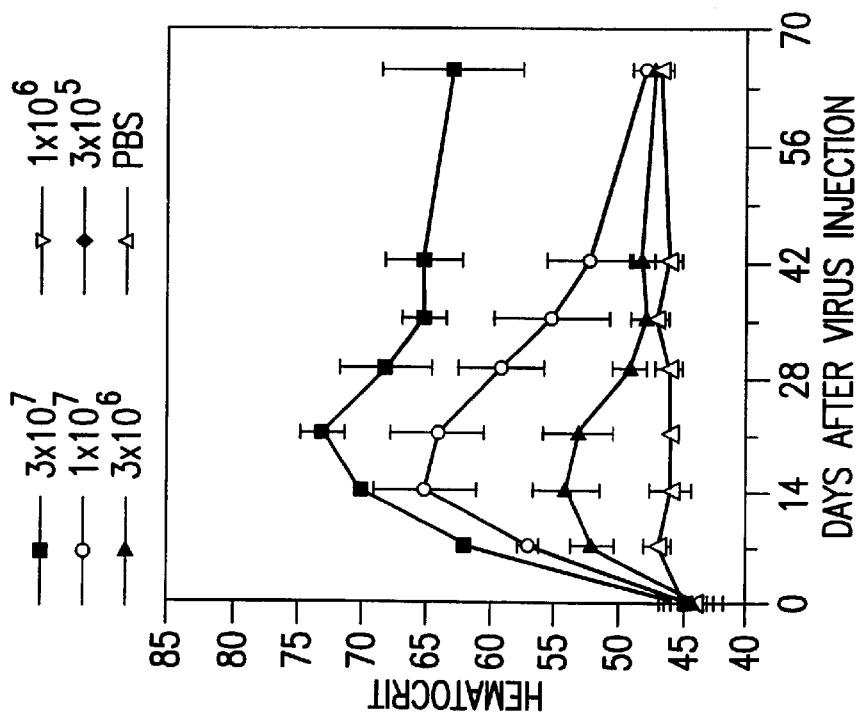
FIG. 3A shows results of experiments in which HVAd-mEPO was injected in the dose range from $3\times10^6$ to $3\times10^7$ pfu (n=5 each).

In mice injected with HVAd-mEPO, the haematocrit initially increased and subsequently decreased in all injection groups (FIG. 3A). For the two lower doses ($3 \times 10^6$ and $1 \times 10^7$ pfu), haematocrit reached control values at day 35 and at day 64 p.i., respectively (FIG. 3A) whereas the haematocrit remained elevated in mice injected with HD-mEPO (FIG. 3B). Interestingly, 64 days p.i. mice infused with $3 \times 10^7$ pfu of HVAd-mEPO had an haematocrit of 62±6.4%, which is not significantly different from the haematocrit of mice injected with 3×10⁵ i.u. of HD(pSTK-ITR-mEPO)Ad (57±5.6% in this experiment). Therefore, the HD vector is roughly 100-fold more effective than a first-generation vector in inducing haematocrit increase in adult immunocompetent BALB/c mice.

We claim:

1. A method for delivering a therapeutic level of erythropoietin to a mammal in need thereof, the method comprising administering to the mammal a helper-dependent adenoviral vector which expresses erythropoietin, wherein the adenoviral vector has had the entire adenoviral genome coding sequence removed and substituted with exogenous stuffer DNA and DNA encoding erythropoietin operably linked to regulatory sequences for expression of erythropoietin, and wherein the adenoviral vector is administered in a dosage from about 1×10³ to 1×10⁶ adenoviral particles/g body weight of the mammal, and erythropoietin expression from the vector provides to the mammal at least 5 mU/ml circulating erythropoietin and an increase in haematocrit of at least 5%.

2. The method according to claim 1 wherein the dosage is about 1×10⁴/g body weight.

3. The method according to claim 1 wherein the step of administering comprises intravenous injection.

4. The method according to claim 1 wherein the mammal is a human.

* * * * *

UNITED STATES PATENT AND TRADEMARK OFFICE
CERTIFICATE OF CORRECTION

PATENT NO. : 6,641,807 B1 Page 1 of 1
DATED : November 4, 2003
INVENTOR(S) : Rocco Savino, Gennaro Ciliberto and Nicola La Monica It is certified that error appears in the above-identified patent and that said Letters Patent is hereby corrected as shown below:

<u>Title page,</u>
Item [73], Assignee, delete "Merck & Co., Inc., Rahway, NJ (US);" and insert
-- Istituto Di Ricerche Di Biologia Molecolare P. Angeletti S.P.A., Pomezia, Roma (IT); --

Signed and Sealed this

Tenth Day of February, 2004

JON W. DUDAS
*Acting Director of the United States Patent and Trademark Office*